United States Patent
Ahmed et al.

(10) Patent No.: US 9,340,778 B2
(45) Date of Patent: May 17, 2016

(54) SINGLE STEP LIQUEFACTION AND SACCHARIFICATION OF CORN STARCH USING AN ACIDOPHILIC, CALCIUM INDEPENDENT AND HYPERTHERMOPHILIC PULLULANASE

(71) Applicants: Nasir Ahmed, Lahore (PK); Naeem Rashid, Lahore (PK); Muhammad Saleem Haider, Lahore (PK); Muhammad Akhtar, Lahore (PK)

(72) Inventors: Nasir Ahmed, Lahore (PK); Naeem Rashid, Lahore (PK); Muhammad Saleem Haider, Lahore (PK); Muhammad Akhtar, Lahore (PK)

( * ) Notice: Subject to any disclaimer, the term of this patent is extended or adjusted under 35 U.S.C. 154(b) by 0 days.

(21) Appl. No.: 14/183,216

(22) Filed: Feb. 18, 2014

(65) Prior Publication Data
US 2014/0227744 A1    Aug. 14, 2014

Related U.S. Application Data

(63) Continuation of application No. 13/765,481, filed on Feb. 12, 2013, now abandoned.

(51) Int. Cl.
| | | |
|---|---|---|
| *C12N 9/28* | (2006.01) | |
| *C12N 9/24* | (2006.01) | |
| *C12N 9/44* | (2006.01) | |
| *C12P 19/02* | (2006.01) | |
| *C12P 19/14* | (2006.01) | |
| *C12P 19/16* | (2006.01) | |
| *C12N 9/26* | (2006.01) | |
| *C12P 19/12* | (2006.01) | |

(52) U.S. Cl.
CPC ............ *C12N 9/2417* (2013.01); *C12N 9/2414* (2013.01); *C12N 9/2457* (2013.01); *C12P 19/02* (2013.01); *C12P 19/12* (2013.01); *C12P 19/14* (2013.01); *C12P 19/16* (2013.01); *C12Y 302/01041* (2013.01); *Y02P 20/52* (2015.11)

(58) Field of Classification Search
None
See application file for complete search history.

(56) References Cited

FOREIGN PATENT DOCUMENTS

| | | | |
|---|---|---|---|
| WO | WO 2011076123 A1 | * | 6/2011 |
| WO | WO 2013048700 A1 | * | 4/2013 |

OTHER PUBLICATIONS

Gantelet et al., Purification and properties of a thermoactive and thermostable pullulanase from Thermococcus hydrothermalis, Appl. Microbiol. Biotechnol., 1998, 49, 770-77.*
Kanai et al., A global transcriptional regulator in Thermococcus kodakaraensis controls the expression levels of both glycolytic and gluconeogenic enzyme-encoding genes, J. Biol. Chem., 2007, 282, 33659-70.
Uniprot, Accession No. Q5JID9, 2005, www.uniprot.ogr.

* cited by examiner

*Primary Examiner* — Robert Mondesi
*Assistant Examiner* — Todd M Epstein
(74) *Attorney, Agent, or Firm* — Sarfaraz K. Niazi

(57) ABSTRACT

A novel thermoacidophilic pullulanase (Tk-PUL) from hyperthermophilic archaeon *Thermococcus kodakaraensis* KOD1 is described here that efficiently hydrolyzes starch under industrial conditions in the absence of any additional metal ions. The gene encoding Tk-PUL was cloned and expressed in *E. coli* cells. The purified recombinant enzyme possesses the following properties: shows both pullulanase and α-amylase activities, displays highest activity at 95-100° C., active over a broad pH range (3.0-8.5) with optimum working pH 3.5, stable for several hours at 90° C. and displays a half-life of 45 minutes at 100° C., activity and stability are independent of calcium and other metal ions, and hydrolyzes maltotriose. Moreover, recombinant Tk-PUL can be used for single step liquefaction and saccharification of corn starch (without any α-amylase or β-amylase) at pH 4.2 in the absence of calcium.

5 Claims, 16 Drawing Sheets

```
   1 atgaaaaaaggtggtctgctgctcattctcctgattctggtctcaatcgccagcggatgt
   1 M  K  K  G  G  L  L  L  I  L  L  I  L  V  S  I  A  S  G  C 61 atctcggagagcaacgaaaatcaaactgcaacggcttcgaccgttccaccgacttcagtg
  21 I  S  E  S  N  E  N  Q  T  A  T  A  S  T  V  P  P  T  S  V 121 acaccctcacagtcttccactcccacaacctcgacctcgacgtacggcccttccgaaaga
  41 T  P  S  Q  S  S  T  P  T  T  S  T  S  T  Y  G  P  S  E  R 181 acggagcttaaacttccttcggttaactacactcccatctacgtcggcatagagaaaggc
  61 T  E  L  K  L  P  S  V  N  Y  T  P  I  Y  V  G  I  E  K  G 241 tgtccctccggaagagtcccggtgaagttcacgtacaaccccggaaacaagaccgtaaag
  81 C  P  S  G  R  V  P  V  K  F  T  Y  N  P  G  N  K  T  V  K 301 tctgtcagcctccgcgggagcttcaacaactggggagagtggccgatggagctgaagaac
 101 S  V  S  L  R  G  S  F  N  N  W  G  E  W  P  M  E  L  K  N 361 ggcacgtgggagacgaccgtctgtctccgccctggaaggtatgagtataagtacttcatc
 121 G  T  W  E  T  T  V  C  L  R  P  G  R  Y  E  Y  K  Y  F  I 421 aacggccagtgggtcaaggacatgtccgacgacgggacgggaaggccctacgaccccgat
 141 N  G  Q  W  V  K  D  M  S  D  D  G  T  G  R  P  Y  D  P  D 481 gcagacgcctatgcccccgatggctacggggaaagaacgccgtgagggtagttgagggc
 161 A  D  A  Y  A  P  D  G  Y  G  G  K  N  A  V  R  V  V  E  G 541 cgcgaagcgttctacgtggagttcgatccaagagacccagcctacctcagcatcgcggac
 181 R  E  A  F  Y  V  E  F  D  P  R  D  P  A  Y  L  S  I  A  D 601 aaaagaaccgtggtcaggttcgaggctaagagagacaccgtcgagtctgcggttctcgtt
 201 K  R  T  V  V  R  F  E  A  K  R  D  T  V  E  S  A  V  L  V 661 acggatcacgggaactacacgatgaagcttcaggtctggtgggacttcggcgaaacctgg
 221 T  D  H  G  N  Y  T  M  K  L  Q  V  W  W  D  F  G  E  T  W 721 cgcgccgagatgccagttgaacccgctgattattacattctcgtaacctcctccgacggc
 241 R  A  E  M  P  V  E  P  A  D  Y  Y  I  L  V  T  S  S  D  G 781 gggaagtttgccgtcctaaacacaagcgaaagcccgttcttccactttgatggcgttgag
 261 G  K  F  A  V  L  N  T  S  E  S  P  F  F  H  F  D  G  V  E 841 gggttccccagctggagtgggtgagcaacgggataacctaccagatattccccgacagg
 281 G  F  P  Q  L  E  W  V  S  N  G  I  T  Y  Q  I  F  P  D  R 901 ttcaacaacggcaataaaagcaacgatgccctagctttggatcacgacgagctaattttg
 301 F  N  N  G  N  K  S  N  D  A  L  D  H  D  E  L  I  L
 961 aaccaggttaatccagggcagccaatcctctccaactggagcgacccgataacgcccctc
 321 N  Q  V  N  P  G  Q  P  I  L  S  N  W  S  D  P  I  T  P  L 1021 cactgctgccaccagtacttcggcggcgacataaagggaataacggagaagctcgactac
 341 H  C  C  H  Q  Y  F  G  G  D  I  K  G  I  T  E  K  L  D  Y 1081 cttcagagcctaggtgttactataatctacatcaacccgattttcctctcgggaagcgcc
 361 L  Q  S  L  G  V  T  I  I  Y  I  N  P  I  F  L  S  G  S  A
```

FIG. 2

```
1141 cacggctacgacacctacgactactaccggctcgaccccaagttcgggaccgaggatgag
 381  H  G  Y  D  T  Y  D  Y  Y  R  L  D  P  K  F  G  T  E  D  E 1201 ctgagagagttcctcgatgaggcccacaggaggggaatgagggtaatcttcgatttcgtg
 401  L  R  E  F  L  D  E  A  H  R  R  G  M  R  V  I  F  D  F  V 1261 cccaaccactgcggcatagggaatccagccttcctcgacgtctgggagaagggcaacgaa
 421  P  N  H  C  G  I  G  N  P  A  F  L  D  V  W  E  K  G  N  E 1321 agcccatactgggactggttcttcgtcaagaagtggcccttcaagctcggcgatgggagc
 441  S  P  Y  W  D  W  F  F  V  K  K  W  P  F  K  L  G  D  G  S 1381 gcctacgtcggctggtggggctttgggagccttccgaagctcaacactgccaaccaggag
 461  A  Y  V  G  W  W  G  F  G  S  L  P  K  L  N  T  A  N  Q  E 1441 gtcagggagtacctgataggagcggccctccactggatagagttcggctttgacggcatt
 481  V  R  E  Y  L  I  G  A  A  L  H  W  I  E  F  G  F  D  G  I 1501 agggtggatgtgccgaacgaagtcctcgacccggggacgttcttcccggagctgagaaag
 501  R  V  D  V  P  N  E  V  L  D  P  G  T  F  F  P  E  L  R  K 1561 gcagttaaggagaaaaagcccgacgcgtacctcgtcggcgagatatggacgctctccccg
 521  A  V  K  E  K  K  P  D  A  Y  L  V  G  E  I  W  T  L  S  P 1621 gagtgggtgaagggagaccgcttcgactccctcatgaactacgccctcgggagggacatc
 541  E  W  V  K  G  D  R  F  D  S  L  M  N  Y  A  L  G  R  D  I 1681 ctcctgaactacgctaagggcctgctcagcggagaaagtgcaatgaaaatgatgggacgt
 561  L  L  N  Y  A  K  G  L  L  S  G  E  S  A  M  K  M  M  G  R 1741 tactacgcttcctacggcgagaacgtagttgcgatgggcttcaacctcgttgattcgcac
 581  Y  Y  A  S  Y  G  E  N  V  V  A  M  G  F  N  L  V  D  S  H 1801 gacacttcgagggttctcactgacctcggtggtggcaaactgggagacacaccgtcaaac
 601  D  T  S  R  V  L  T  D  L  G  G  G  K  L  G  D  T  P  S  N 1861 gagtcaattcagaggctcaagctcctctcaacgctcctctatgccctgcccggaactccc
 621  E  S  I  Q  R  L  K  L  L  S  T  L  L  Y  A  L  P  G  T  P 1921 gtcaccttccaggggacgagaggggactgctcggagacaagggacactacgatgagcaa
 641  V  T  F  Q  G  D  E  R  G  L  L  G  D  K  G  H  Y  D  E  Q 1981 cgctatccgatacagtgggatactgtgaacgaggacgtcctgaaccactacagggcactg
 661  R  Y  P  I  Q  W  D  T  V  N  E  D  V  L  N  H  Y  R  A  L 2041 gcggagctcagaaaaagagttcccgcattgaggagcagcgcaatgaggttctacactgcc
 681  A  E  L  R  K  R  V  P  A  L  R  S  S  A  M  R  F  Y  T  A 2101 aaaggcggcgttatggccttcttcaggggacatcatgacgaggttctcgtcgttgccaac
 701  K  G  G  V  M  A  F  F  R  G  H  H  D  E  V  L  V  V  A  N 2161 agctggaagaagccagccctactggagcttcccgagggagagtggaaagtaatctggcct
 721  S  W  K  K  P  A  L  L  E  L  P  E  G  E  W  K  V  I  W  P 2221 gaggatttcagcccggaactgcttcgcggcacagttgaagtgccagccatagggataatc
 741  E  D  F  S  P  E  L  L  R  G  T  V  E  V  P  A  I  G  I  I 2281 atccttgagcggggttga
 761  I  L  E  R  G  *
```

FIG. 2 (Cont'd)

```
T.kod   ------------------------------------------------------------  1
T.agg   ------------------------------------------------------------  1
T.gam   ------------------------------------------------------------  1
T.AM4   ------------------------------------------------------------  1
P.cal   ------------------------------------------------------------  1
D.kam   MIKLRKLILATISLLLITSILQPLVPMANSAGDKIYVAIVWHYHQPWYYSVDESYLVLPW   60
D.muc   ------------------------------------------------------------  1

T.kod   ---------------------------------------MKK--GGLLLILILLVSIASGCI  21
T.agg   ---------------------------------------MRRRFGALLMMEMLNIJASGCL  23
T.gam   --------------------MSKTLIYPFLYSLLVIHVGKNVVLALIFLLIGGVTAAGCL   40
T.AM4   ---------------------------------------MGRKVALALLLLLIGGVLAAGCL  23
P.cal   ------------------------------------------------------------  1
D.kam   VRMHSVGNYYKMAHILSKYPDIRVSFTFSGSLLEQLIDMVENNKMDVREILSWRVVNCTL  120
D.muc   ------------------------------------------------------------  1

T.kod   SESNENQTAT----------------ASTVPPTSVTPSQSSTPTTSTSTYGPSERTELKL   65
T.agg   QS--------------------------------PTT----------QELKL          33
T.gam   GGGSNGASTTSGFSQTTSSTTTTVSSCSTSTYSTTTSTIS--TTTQTSQTTTSPTATPS   98
T.AM4   GGGTSKTSSSPISQSSTTAVPSTTTESTTSTQYSTTTTSTTSITTTTTTESTATATTTPT  83
P.cal   ------------------------------------------------------------  1
D.kam   SREDVFKMLQIPGGFFDVNWGRIVDKSPRFSELRSLAQSAWSQCSQITRSESELMNCIVD 180
D.muc   ------------------------------------------------------------  1

T.kod   PSVNYTPIYYG--IEKGCPSGRVPVKFTYNPGNKTVKSVSLRGSFNWCEWPMELK-NGT  122
T.agg   PSGNYPPIYINEKSQNMCPPGKVPVTFRYCP-EENVTSVSLRGSFNDWGELPMKNE-NGT   91
T.gam   PGPGYKVIYLT-TSSGSCPSGKIPVEFVYNPGNKTVKRVSLRGTFNDWSQWLMCKKPDGR 157
T.AM4   PAREYRVIYLS-GSSGSCPEGKVPVEFVYDPGNKTVKMVSLRGTFNCWSQWLMHKKPDGK 142
P.cal   ------------------------------------------------------------  1
D.kam   RFTGGNLSSQNVVDLAVLFNLLWIDPQVSQEEYPEVYSLMERAYTSSQPNYTINELRIVL 240
D.muc   --MGWRPVAYY--------ATLILVLLQLTP--------LP------------------  23

T.kod   WETTVCLRPGRYEYKYFINGQWVKDMSDDGTGRPYDPDADAYAPDGLGGKNAVRVEGRE  182
T.agg   WVRTVCLNPGRYEYKFFVDGPWIKDMS------AVDPTADAYVDDGRGGKNAVKIVKGEQ 145
T.gam   WVLRICLAPGTYEYKFYVDGHWIKDMS------KADPTADKYVDDGRGGKNAVKLVGCAS 211
T.AM4   WYLRICLKPGTYEYKFYVDGHWIEDMS------KADPTADGYVDDGRGGKNAIKVVKGES 196
P.cal   ------------------------------------------------------------  1
D.kam   NTHRDIMAKIISAYKELALKEQVELVPVPYSHPLAPIIADLGFSEDLEIHISESMRLFKE 300
D.muc   ---------------------------------------IACASIMEIYVADD       37

T.kod   AFYVEFDPRDPAYLSIADKRTVVREEAKRDT-VESAVLVTDHGNYTMKLQVWWDFGETWR 241
T.agg   GLITEHDPKNPAYLSIADNRTVIRFKVQPNQ-IQSAFLVASNGEYKMERQLWWGSGEVWR 204
T.gam   SLVIEHOPIDPAYLSIADTRTVIREEVNPGL-VDSAVLVTTIGNFTMEKQVWWDSGEVWR 270
T.AM4   ALKIEHNPIDPAYLSIADNRTVVREEVDPCL-VSAVLVTTIGNFTMEKQVWWDSGEVWR  255
P.cal   --------------------MSKKLPLLLVVLSAVLLYAQG-------------------  21
D.kam   YFNVTPRGVWPAEEAVNEEVLEAFKRAGVTWTITDESILGKTGVNTGDINVLGIPWYIDF 360
D.muc   QVTVVHNPIDPAYLSAADGYLIPRIRVASSLDVASGTLVADKCEYQLKPQLATNTWRVYY  97

T.kod   AEMP----VEPADYYILVTSSDGG--------------------KFAVLNTSESP     272
T.agg   VEIQE----VSPIEYYFKLTTNNG--------------------EVLVTNTSKNP     235
T.gam   AELP-----VGSFDYHFVLN-VNGT--------------------EFIVLNSSESP    300
T.AM4   AELP-----VRAFDYHFVLD-VNGT--------------------EFVVLNSSKAK    285
P.cal   --------------------------------VFVVQSATDF                  31
D.kam   QEGRIYVVFRDTELSNLISFQYSSQSYTNAVNDFINRVLSLKASASGPRITVVALDGENP 420
D.muc   ATIPIGEASRGLNYYFKLTLRNNT--------------------VVYVYNATASR     132
```

FIG. 3

```
T.kod   FFHFDGVEGFPQ----------LEWVSNCITYQIFPDRENNGNKSNDALALDHDELILN 321
T.agg   FFTEDGINFFPQ----------VEWVSKCIGYQIFPDRFNNGOPSNDALALQTDEGWFN 284
T.gam   ELHFDGVNRFPQ----------IEWVSSAIGYQIFPDRFENGNHSNDALALDHDELVIN 349
T.AM4   YFHFDGTNRFPQ----------LEWVSRAIGYQIFPDRFFNGNRSNDALALDHDELIYN 334
P.cal   TGDYKCPGRELP----------PQNP----------VFKNG----TVFDLTRFEVLYN 65
D.kam   WENYERFGDLFLNELYRRLSELQAQCVLETITPDSFIDLFPNVAQPLPLKTYVYLDIAGK 480
D.muc   LFNENCSIVERQ----------VEWVKSRVGYQIFPDRFYNGDPSNDLKANLTDELWIN 181
T.kod   QVN--------------------------------------------------------- 324
T.agg   ELI--------------------------------------------------------- 287
T.gam   ELT--------------------------------------------------------- 352
T.AM4   QMF--------------------------------------------------------- 337
P.cal   ATA--------------------------------------------------------- 68
D.kam   DTSNIPGNSYGDGYSELPRKAVQAHIPEGSWSGGEVATWIGDRQENIAWMWLVKARSEIM 540
D.muc   EVS--------------------------------------------------------- 184

T.kod   ------PGCPILSNWSDPITPLHCCHQYFGGDIKGITEKLDYLQSLGVTIIYLNPIFLSG 378
T.agg   ------NERPILSNWSDPISPLHCCHQYFGGDIKGIIEKLDYLQELGVIVIYLNPIFLNG 341
T.gam   ------NEKPILSNWSDPITPLHCCHQYFGGDIAGITEKLDYLSSLGVRLIYLNPIFLSG 406
T.AM4   ------NEKPILSNWSDPITPLHCCHQYFGGDIAGITEKLDYLSSLGVKLIYLNPIFLSG 391
P.cal   ------DALVERLTFADLGDNPWGTETGFS----------------VQYIQIYIHRGFPG- 106
D.kam   RKLGIQDFKSIYVQYPEIARSILKALASDWWWWYGGDGGGSPQTFDPLFKAYLRFA-QLA 600
D.muc   ------RGVPVFTRWDCFVTSLHCCHQYFGGDLKGVTEKLDYLKELGVGLIYLNPIFLSG 238

T.kod   SAHGYDTYDYYR DP------------------------------KFGTEDELRE 403
T.agg   SAHGYDVYDHYR DP------------------------------QFGSEEDLKI 366
T.gam   SVHGYDTYDYYR DP------------------------------KFGTETELKL 431
T.AM4   SVHGYDTYDYYR DP------------------------------KFGTEALKL 416
P.cal   --NPWGTVSCTILRP------------------------------DDGDVAAGNA 129
D.kam   GLTPPDYLDVTAYPDGTPIGVLNTNVPRPSTYTPNIDGIIEQQWYKEISNGNGLRIPVGQ 660
D.muc   SVHGYDTYDYYTVDP------------------------------KFGTLEDLKT 263

T.kod   FLDEAHRRGMRVIFDFVPNHCGIGNPAFLDVWEKGNESPYWDWFFVKKWPFKLGDCSAYV 463
T.agg   LTEEAHRRGIRIIFDFVPNHSGIGHWAFLDVASRGKKSPYWNWFEVQRNPFKLGDCKAYL 426
T.gam   FLSEAHRRGIKVIFDFVPDHSGICADQFLDVWKNGRESQYWMWYEIKRWPFKLGDGSAYE 491
T.AM4   FLTEAHRRGIRVIFDFVPDHSGICAEQFLDVWKNGRKSPYWHWYFIIKRWPFKLGDGSAYE 476
P.cal   FFDEATR--------FFCPDPANLTQFKYTPGVKFSNDAPWDVAIEIG-------------- 169
D.kam   VLDSLLILVEPGKLYEALNLTTVDTRGLRIGIYFSSPSTSLSPFNPGYQVYPRNSRVDLG 720
D.muc   LINEAHRRGIKVIFDFVPDHVGLGFWAFQDVYRNGRNSTYWSWFIVYKWRFKLGDPTAYK 323

T.kod   GWWGTGSLPKLNTANQEVREYLIGAALEWLEFGFDG----IRVDVFNEVLDPGTFFEELR 519
T.agg   GWWGTGSLPKLNTANPEVKSYLIGAALHWLDFGFDG----IRIDAFQBLINAEEFFSELR 482
T.gam   GWWGTGSLPKLNTANPEVRFYLIGSALKWLDFGFDG----IRVDTPADLVNADEFFREER 547
T.AM4   GWWGTGSLPKLNTANPEVADYLEGAAMKWLDFGFDG----IRVDTPADLVNADEFFREER 532
P.cal   PKWCNETVNYVAVADVTGGTISVAPLQRVYASGNTI----VAVVPRSAIPPTTRLMSDFP 225
D.kam   IYLVKEILVDVAARTVTISNASVNDWNEVWRGNVSVNAGGSSTTAEFSIDTTELNLPEGA 780
D.muc   CWWGTGSLPQLNVLNTEVROYLINVALYWLSIGFDG----LRIDTELDVIDSESFFRELR 379

T.kod   KAVKEKKPDAYLVGEIWTLSPEWVKGDRFDS-----------------------LMNY 554
T.agg   KAIKEKHPDAYLVGEIWELSPRWVQGNMFDS-----------------------LMNY 517
T.gam   ERVKERHPNAYLVGEIWTLSPEWVKGDKFDS-----------------------LMNY 582
T.AM4   ERIKERHPDAYLVGEIWTLSPEWVKGDKFDS-----------------------LMNY 567
P.cal   Q----------------PSWRYYVLVTS-----------------------YDGY 241
D.kam   TTYLAVVLYSGDNVTEYSSRFGLVYQLDIPRGAISGTIIFEMNDPTGDDDGPGGYGYPGN 840
D.muc   EAVKSRYPDAYLVGEIWDYRPEWLRGNAFDS-----------------------LMNY 414
```

FIG. 3 (cont.)

```
T.kod   ALGRDILLNYAKGLLSGESAMKMKGRYYASYGENVVAMGFNLVCSHDTSRVLTDLGGGKL  614
T.agg   ALGRDILLAYARGDWNGERTLELLGRYYASYGENVIAMGFNLVSSHDTSRVLTDLGGGNL  577
T.gam   ALGRDILLRYARGILSGKTALNLLGKYYASYGENVVAMGFNLVCSHDTSRVLTDLGGGKL  642
T.AM4   ALGRDILLRYARGILSGKTALNLLGRYYASYGENVVAMGFNLVCSHDTSRALTDLGGCEL  627
P.cal   GPCR---------------IRPBCPMAQEWAVGVGAANASSVLAGTVPRVLDVLC---P  282
D.kam   SVFKPGVTDMIRFTVIDQGDKIVFKVIFRDLCGNPWSGPNGWSLQQVHIYIHTPLCRKGN  900
D.muc   YLGRNILLSYARGALNGYTASMKLAEYYAGIGVNVAGMGFNIICSHDTSRVLTDLGGGGL  474

T.kod   GDTPSNESICRL------KLLSCLLYALPGIPVTFQGDERGCLGDKCHIDEQRYPIQWDT  668
T.agg   GDTPKPEAICRL------KLLSCLLYTLPGMPVTFQGDERGCLGDKEHFDSHRYPIQWDT  631
T.gam   GDKPKPEAVKRL------KLLSALLYTLPGMPVTFQGDECGILGDKNHIDEQRYPIQWSE  696
T.AM4   GEEPKPEAVKRL------KLLSCLLYTLPGMPVTFQGDECGCLGDKNHIDEQRYPIQWDE  681
P.cal   NTPLATFTRNSS------ATLPSTTLAWGNEPLAVTTTTVNRILPVTATKTATLTITETS  336
D.kam   STTIGLNADIAEGYEWHMALILAPGWGSDPIPVGEKSAIYYYDKDKPVVQDSGTKVYADQ  960
D.muc   NSTPSNEBIARL------KLLSTLQYTQPGMPVVFQGDERGITCRQGNHDEQRYPIQWDR  528

T.kod   VNEDVLNHYRA-------------LAELRKRVPALRSSAMRFYIAKGGVIAFFRGHHDEV  715
T.agg   VNEDVLNHYKS-------------LADLRKSVPALTSSKIKFYTSKEGVLAFFRGHDDEV  678
T.gam   CNVSLVEHYRS-------------LGKLRESIPALSSSKISFYMAKDGVIAFFRGHRNEI  743
T.AM4   CNTSLVEHYRS-------------LGKLRESVPALTSSKISFYMAKDGVIAFFRGHGNEV  728
P.cal   FVTRTVTQTQQ-------------VIQPVVDPMSYVVMGIGVVAGLVGAIAAARRK----  379
D.kam   AGNSIIAEVSKSLLYDVEDIKKWVYIVAVTSHDGYGTNKIRSFSPSGGEWSVSVPSNYSV  1020
D.muc   LNVEVYEHYKR-------------LGELKNTIPALSTSILHVLGGSGGLIAYTRGYMDEV  575

T.kod   LVVAN-SWKKPALLELPECEWKVIWPED--FSPELLRGTVEVPAIGIIILERG-------  765
T.agg   LVIAN-NVPKDTSIPLPPGKWKQIWPE----GEKIFEKEITVPGLEVLVLVKT-------  726
T.gam   LVVAN-NRDSPTSIPLPSGTWKEAWPG-----NGSYQNSLEVPPVSLIVLRRG-------  790
T.AM4   LVVAN-NGEARAEIPLPPGTWEEVWPG-----SGSYSNSLDVPPVSLIVLRRG-------  775
P.cal   ------------------------------------------------------------  379
D.kam   AILAGVIPYILDVLAPTPEEQHSMLLSFDLAGKKLAQLKGYGATPVTITTTPVTTTTTTT  1080
D.muc   LVIANNDASTPQSYELPPGNWTLLYASNNWSEVSVEHNTVIVPPLTALILVRNTVSETTT  635

T.kod   ------------------------------------------------------------  765
T.agg   ------------------------------------------------------------  726
T.gam   ------------------------------------------------------------  790
T.AM4   ------------------------------------------------------------  775
P.cal   ------------------------------------------------------------  379
D.kam   TTTATTTTTTTTTTPTTTTTTTTTTTTTPIQQPLLNMGLLVTLVVVIIVVAAILIYLFRT  1140
D.muc   TSTAVTSFPGTMYTETTAIPGRLEQDTRVLIIVVAVPLLLATLVLLRRHRA---------  686

T.kod   ----- 765
T.agg   ----- 726
T.gam   ----- 790
T.AM4   ----- 775
P.cal   ----- 379
D.kam   KTGKS 1145
D.muc   ----- 686
```

FIG. 3 (cont.)

| Enzyme source | Region I<br>Pos. 412-423 | Region II<br>Pos. 498-507 | Region III<br>Pos. 526-538 | Region IV<br>Pos. 598-607 |
|---|---|---|---|---|
| | # | | # | # |
| Q5JID9 | GMRVITDFVPNH | DGIRVDVPNE | PDAYLVGEIWTL | DSHDTSRVLT |
| Q9P9A0 | GIRIITDFVPNH | DGIRIDAPQE | PDAYIVGEIWEL | SSHDTSRVLT |
| Q9HHB0 | GIKVIFDFVPDH | DGLRIDTPLD | PDAYIVGEIWDY | GSHDTSRVLT |
| P32818 | GIKVMLDAVFNH | DGWRLDVANE | PDLYIIGEIWHD | GSHDTPRILT |
| P29964 | GIKVITDAVFNH | DGWRLDVANE | PEAIIVGEVWHD | GSHDTERFLT |
| Q08751 | GIKIILDAVFNH | DGWRLDVANE | PDALIVGEIWHD | DSHDTERFLT |
| P38940 | GIRVMLDAVFNH | DGWRLDVANE | PDVYILGEIWHD | GSHDTSRILT |
| Q57482 | GIRVMLDAVFNH | DGWRLDVANE | PDVYILGEVWHD | GSHDTPRILT |
| Q45490 | AIRVMLDAVFNH | DGWRLDVANE | PDAYIIGEIWHD | GSHDTPRILT |
| Q819G8 | GIKVMLDAVFNH | DGWRLDVANE | PEVYILGEIWHD | DSHDTPRILT |

Fig. 4

SINGLE STEP LIQUEFACTION AND SACCHARIFICATION OF CORN STARCH USING AN ACIDOPHILIC, CALCIUM INDEPENDENT AND HYPERTHERMOPHILIC PULLULANASE

CROSS REFERENCE TO RELATED APPLICATION

This application is a continuation of U.S. patent application Ser. No. 13/765,481, entitled "Single Step Liquefaction and Saccharification of Corn Starch Using an Acidophilic, Calcium Independent and Hyperthermophilic Pullulanase" filed on Feb. 12, 2013, the contents of which are incorporated herein by reference in its entirety.

FIELD OF INVENTION

The present invention is within the field of thermostable amylases. More specifically, the present invention relates to a novel hyperthermostable pullulanase having an acidic pH optima and no metal ion requirement. Moreover, it relates to methods of producing the pullulanase and use of this enzyme in simultaneous liquefaction and saccharification of starch.

DESCRIPTION OF THE PRIOR ART

The most abundant storage polysaccharide i.e., starch is a polymer of anhydro glucose units. Its major utilization is in the production of sweeteners. These sweeteners may be solids like glucose (dextrose), maltose and fructose or they may be liquids like glucose syrup, maltose syrup and high fructose corn syrup. Glucose/glucose syrup is either used directly in the production of various foods or used as raw material in other biotechnological processes for the production of sorbitol, citric acid, amino acids and fuel ethanol (Crabb and Mitchinson, 1997; Crabb and Shetty, 1999; Ibeto et al., 2011).

For production of glucose/glucose syrup corn starch is hydrolysed in two-steps, liquefaction and saccharification, which involve a number of starch hydrolyzing enzymes like α-amylase, glucoamylase/α-glucosidase and pullulanase. During liquefaction α-amylase splits starch into varying lengths of polysaccharides in the presence of calcium (40 ppm) at a temperature of 95-105° C. and pH about 6. During saccharification α-glucosidase and pullulanase are used that hydrolyze the polysaccharides to monosaccharides (glucose) at a temperature of 60-65° C. and pH close to 4.5 (Lêveˆque et al., 2000). For liquefaction concentrated suspension of corn starch (30-35%) is prepared, pH is increased from 4.5 (natural pH of starch slurry) to 6.0 and calcium is added. α-amylase is then mixed and suspension is heated to 105-110° C. and held at this temperature for 5-10 minutes. The temperature is then lowered to 90-95° C. and liquefaction is completed at this temperature in 1-2 hours. For saccharification both pH and temperature of the liquefied starch are lowered to the optimal pH (4.5) and temperature (60-62° C.) of the saccharifying enzyme and process is completed under these conditions in 72-96 hours.

Though pH adjustment before and after liquefaction step increases the cost of process but is necessary because currently available liquefying enzymes (α-amylases) are unable to work efficiently below pH 5.9 (Van der Maarel et al., 2002). Furthermore, for efficient amylolytic activity starch granules should be completely gelatinized which is only possible above 100° C. Therefore the starch-processing industry needs thermostable and acid-stable amylases to decrease the cost of glucose-production. They would help in completing the processes quickly and efficiently as wastage of chemicals in pH adjustment and time in cooling processes will be avoided.

Another major problem for starch industry arises during conversion of glucose syrup to high fructose syrup. Starch liquefying enzymes require calcium for their activity and thermostability but this added calcium inhibits the activity of xylose isomerase (commonly known as glucose isomerase). This enzyme is used for isomersation of glucose to fructose syrup (Wang et al., 2007). Furthermore, calcium oxalate is produced as a waste product which deposits in the pipes and heat exchangers. This deposition chokes them and increases the production cost. With the development of calcium independent, thermostable and acid stable enzymes this problem can be solved.

Thermostable amylases were previously isolated from Bacillus species especially from *B. licheniformis*, *B. amyloliquefaciens* and *B. subtilis* (Underkofler, 1976). TERMAMYL® (NOVO NORDISK A/S Denmark) is a thermostable α-amylase produced from *B. licheniformis*. It has an optimal temperature of 90° C. and requires additional calcium for its thermostability. *B. stearothermophilus* α-amylase disclosed in U.S. Pat. No. 4,284,722 shows superiority over *B. licheniformis* amylase in respect of lower pH optima but it is also not suitable for starch liquefaction below pH 5.0.

Another important liquid sweetener, maltose syrup, is a concentrated and purified solution containing major proportion of maltose with respect to other saccharides but maltose content not less than 30% of the solution on dry basis. The preparation of maltose syrup by the action of a combination of amylolytic enzymes has previously been disclosed in U.S. Pat. No. 3,565,765 (maltogenic amylase and pullulanase), U.S. Pat. Nos. 3,795,584 and 3,804,715 (beta-amylase and alpha-1,6 glucosidas/pullulanase), U.S. Pat. No. 3,791,865 (beta-amylase and amylo-1,6 glucosidase), U.S. Pat. No. 3,549,496 (*Bacillus polymyxa* amylase and glucoamylase), U.S. Pat. Nos. 3,832,285; 4,032,403; 3,996,107; 3,998,696 and 4,113,509 (alpha amylase and beta-amylase). There is no report of using a single enzyme for simultaneous liquefaction and saccharification.

During past three decades hyperthermophilic archaea attracted the researchers because their enzymes show extreme thermostability. Recently, several hyperthermostable amylolytic enzymes have been reported from *Pyrococcus furiosus*, *Pyrococcus woesei* (U.S. Pat. No. 5,370,997), *Thermococcus litoralis* (Brown and Kelly, 1993), *Thermococcus aggregans* (Canganella et al., 1994) and *Thermococcus kodakaraensis* KOD1 (Murakami et al., 2006). The genes encoding some of these enzymes have been cloned. For example intra and extracellular α-amylases from *P. furiosus* (Laderman et al., 1993; Dong et al., 1997), *Pyrococcus sp.* KOD1 (Tachibana et al., 1996), *T. profundus* (Lee et al., 1996), *Sulfolobus acidocaldarius* (Kobayashi et al., 1996a), *Sulfolobus solfataricus* (Kobayashi et al., 1996b) and *T. aggregans* (Niehaus et al., 2000). α-amylase from *P. furiosus* (U.S. Pat. No. 5,370,997) has been reported to be independent of calcium requirement with pH optima between 4.0-6.0.

We describe here a novel pullulanase (Tk-PUL) from hyperthermophilic anaerobic archaeon *Thermococcus kodakaraensis* KOD1 that is capable of simultaneous liquefaction and saccharifaction of starch slurry at 90° C. and pH 4.2 in the absence of calcium or any other metal ion without the addition of any liquefying α-amylase and saccharifying β-amylase.

BRIEF SUMMARY OF THE INVENTION

A 2298 bp nucleotide sequence coding for Tk-PUL was identified in the genome of *T. kodakaraensis* KOD1, amplified by polymerase chain reaction and cloned in expression pET-21a(+) (SEQ ID NO. 1). The amino acid sequence of Tk-PUL shared only a 62% or less identity with already known sequences of amylolytic enzymes (SEQ ID NO. 2). Maximum identity (62%) was with pullulan hydrolase III from *T. aggregans*. Recombinant Tk-PUL was produced in *E. coli* and purified to apparent homogeneity on SDS-PAGE. Specific activity of purified Tk-PUL was 70.5 U/mg using pullulan as a substrate. Molecular mass of Tk-PUL was found to be 84402.053 Da by Matrix Assisted Laser Desorption Ionization-Time of Flight Mass Spectrometry (MALDI-TOF MS). Size exclusion chromatography revealed that the recombinant Tk-PUL was a monomer. The recombinant enzyme possessed both pullulanase and α-amylase activities. Highest activities were observed at 95-100° C. Although the enzyme was active over a broad pH range (3.0-8.5), the pH optimum for both activities was 3.5 (in acetate buffer) and 4.2 (in citrate buffer). Tk-PUL was stable for several hours at 90° C. Half-life at 100° C. was 45 minutes (when incubated either at pH 6.5 or 8.5). The enzyme was also stable over a pH range of 4.2-8.5. Calcium ions were not required for activity and stability of recombinant Tk-PUL. Addition of divalent cations such as $Mg^{+2}$, $Mn^{+2}$, $Co^{+2}$ and $Zn^{+2}$ had no effect on the enzyme activity while $Ni^{+2}$, $Cu^{+2}$ and $Fe^{+2}$ exhibited slight inhibitory effect.

One embodiment of the present invention comprises a novel pullulan hydrolase type III (Tk-PUL) comprising an amino acid sequence having at least 65%, 85%, 90%, 98%, or 99% homology to the amino acid sequence of SEQ ID NO:2; a molecular mass of 84.4 kDa; both pullulanase and α-amylase activities; a temperature optimum between 95-100° C. (at pH 4.2 and 6.5); a pH optimum 3.5 (in acetate buffer) and 4.2 (in citrate buffer); a residual activity of 90% after 10 hours incubation (in the absence of substrate) at 90° C.; a half-life of 45 minutes at 100° C. (when incubated in the absence of substrate either at pH 6.5 or 8.5); an independence of calcium ions for activity and stability; an ability to hydrolyze maltotriose into maltose and glucose; and an ability to hydrolyze α-1,4 glycosidic linkages in pullulan in addition to α-1,6 linkages.

Another embodiment comprises a composition comprising an isolated peptide molecule having at least 95%, 98%, or 99% sequence identity to the amino acid sequence of SEQ ID NO 2.

Another embodiment comprises the pullulan hydrolase encoded by SEQ ID NO 1, as well as expression vectors and host cells for expressing the encoded protein.

Another embodiment of the present invention comprises a process for the simultaneous liquefaction and saccharification of starch comprising adding the pullulan hydrolase type III sequence having at least 65%, 85%, 90%, 98%, or 99% homology to the amino acid sequence of SEQ ID NO:2 to a starch solution, adjusting the temperature of the solution to about 100° C. for 10 minutes; lowering the temperature to 90° C. until both liquefaction and saccharification are complete; and wherein the pullulan hydrolase performs both pullulanase and α-amylase activities.

In a further embodiment the process can be carried out at a pH of about 4.2 throughout the process and both liquefaction and saccharification are carried out without the addition of calcium or any other metal ions.

Another embodiment comprises a process wherein liquefaction of a starch solution proceeds in the presence of the pullulan hydrolase described above at a pH of about 4.2 in the absence of calcium followed by saccharification of the liquefied starch by *Aspergillus niger* glucoamylase without pH adjustment.

Tk-PUL was able to hydrolyze a variety of substrates including cyclodextrins and smaller linear oligosaccharides such as maltoheptaose to maltotriose. Final products of hydrolysis (from long chain and small chain saccharides) consisted of a mixture of maltotriose, maltose and glucose. Recombinant Tk-PUL displayed the novel property to hydrolyze maltotriose into maltose and glucose. The end product of pullulan hydrolysis was a mixture of maltotriose, maltose, panose and isomaltose. Tk-PUL is, therefore, proposed as pullulan hydrolase type III though it was previously annotated as pullulanase type II in the genome of *T. kodakaraensis*.

Tk-PUL was able to produce maltose syrup (containing more than 50% of mono-, di- and tri-saccharides) from the hydrolysis of corn starch at 90° C. and glucose syrup (containing more than 90% glucose). It is important to note that the experiments were conducted throughout at pH 4.2 (the natural pH of starch slurry) in the absence of calcium. The recombinant Tk-PUL efficiently liquefied the corn starch in the absence of any liquefying α-amylase. In addition it was able to saccharify (in the absence of β-amylase) the liquefied starch into a mixture of maltotriose, maltose and glucose.

DESCRIPTION OF THE DRAWINGS

FIG. 2: Nucleotide (top) and deduced amino acid (below) sequences of Tk-PUL. A signal peptide of 17 amino acids is double underlined.

FIG. 3: Alignment of Tk-PUL with other archaeal pullulanases. Gaps are shown by dashes, identical residues are shown in white with black background and similar residues are shown in black with gray background. The sequences used in alignment were: T kod, Tk-PUL from *Thermococcus kodakaraensis* KOD1 accession number Q5JID9, T agg, Pullulan hydrolase type III from *T. aggregans* accession number Q9P9A0, T gam, Pullulan hydrolase type III from *T. gammatolerans* accession number C5A115, T AM4, pullulanase type II from *Thermococcus* sp. AM4 accession number B7R259, P cal, Pullulanase from *Pyrobaculum calidifontis* accession number A3MUT4, D kam, pullulanase from *Desulfurococcus kamchatkensis* accession number B8D2L1, D muc, pullulanase from *D. mucosus* accession number Q9HHB0.

FIG. 4: Regions conserved among pullulanases and other amylolytic enzymes. Three acidic residues essential for catalytic activity are marked by #, identical residues are shown in white with black background and similar residues are shown in black with gray background. Swiss-Prot accession numbers of sequences were used i.e., Q5JID9 (Tk-PUL); Q9P9A0 (Pullulan hydrolase type III form *T. aggregans*); Q9HHB0 (Pullulanases from *D. mucosus*); P32818 (Maltogenic α-amylase from *B. cidopullulyticus*); P29964 (Cyclomaltodextrin hydrolase from *Thermoanaerobacter ethanolicus*); Q08751 (Neopullulanase from *Thermoactinomyces vulgaris*); P38940 (Neopullulanase from *B. stearothermophilus*); Q57482 (Neopullulanase from *Bacillus* sp.); Q45490 (Maltogenic amylase from *G. stearothermophilus*); Q819G8 (Neopullulanase from *Bacillus cereus*).

DETAILED DESCRIPTION OF THE INVENTION

Cloning of Tk-Pul Gene

Figure 1:
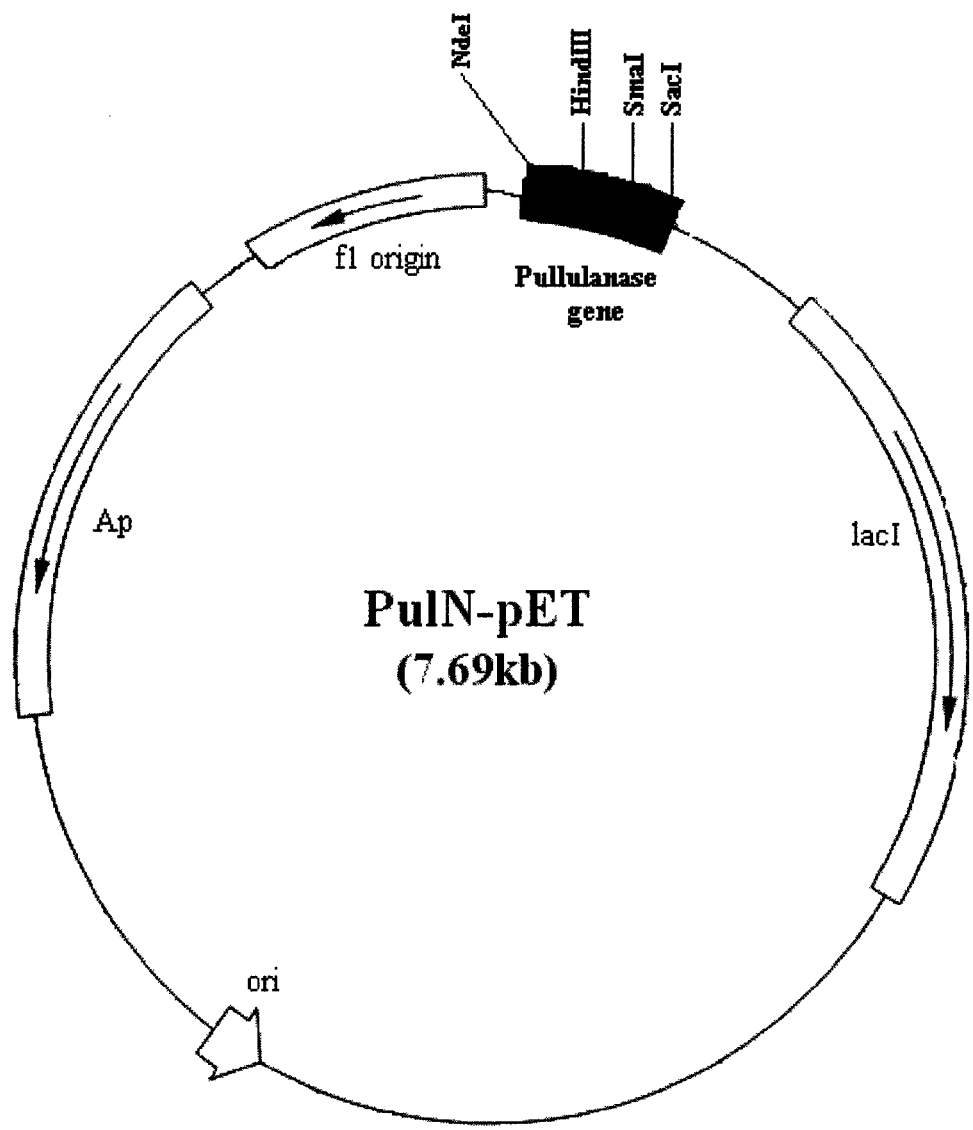
FIG. 1: Schematic diagram of recombinant plasmid PulN-pET representing restriction enzymes that have recognition sites within the pullulanase gene.

The hyperthermophilic archaeal strain KOD1, isolated form Kodakara Island, Kagoshima, Japan, was cultured at 85° C. and cells were obtained. Chromosomal DNA of strain KOD1 was prepared by the method of Ramakrishnan and Adams (Ramakrishnan and Adams, 1995). A 2298 bp open reading frame (ORF) coding for a pullulanase type II of GH13 family was identified in the genome of *T. kodakaraensis* KOD1. A set of primers (5'-CATATGAGCGGATG-TATCTCGGAGAGCAACG-3' (SEQ ID NO 3, corresponding to 5' end of gene) and 5'-GAAGCGGGGGTCAAC-CCCGCTCAAG-3' (SEQ ID NO 4, corresponding to 3' end of the gene) was synthesized. Restriction site of enzyme NdeI (CATATG) was introduced in the forward primer. The gene was amplified by polymerase chain reaction (PCR) using this pair of primers and genomic DNA of *T. kodakaraensis* KOD1 as template. PCR mixture (50 μL) composed of *T. kodakaraensis* KOD1 genomic DNA (100 ng), 1× PCR buffer (0.01% Tween 20, 20 mM $(NH_4)_2SO_4$, 75 mM Tris-Cl pH 8.8 at 25° C.), KCl (50 mM), $MgCl_2$ (2 mM), deoxyribonucleoside triphosphates (dNTPs, 250 μM), forward and reverse primers (100 pmol each), and Taq DNA polymerase (5 units). DNA was amplified in Eppendorf Master Cycler. PCR conditions were: initial denaturation at 94° C. for 2 minutes; followed by 30 cycles of: denaturation at 94° C. for 30 seconds, annealing at 55° C. for 30 seconds, extension at 72° C. for 90 seconds; and final extension at 72° C. for 10 minutes. After completion of PCR the amplified product was analyzed by gel electrophoresis and purified. The amplified DNA fragment was then ligated into T/A cloning vector pTZ57R/T (Fermentas) and used to transform *E. coli* DH5α cells. This recombinant plasmid containing pullulanase gene was named PulN-pTZ. Recombinant plasmid PulN-pTZ was digested with NdeI and BamHI to liberate pullulanase gene which was purified and subsequently ligated between NdeI and BamHI restriction sites of pET-21a(+) (Novagen). The resulting recombinant expression vector was named PulN-pET. Restriction map of PulN-pET is shown in FIG. 1.

DNA Sequence Analysis

The presence of pullulanase gene in recombinant expression vector was confirmed by DNA sequencing using CEQ800 Beckman Coulter sequencing system. Multiple sequence alignment was performed by using ClustalW in BioEdit Sequence Alignment Editor (Hall, 1999).

Gene Expression and Purification of Recombinant Tk-PUL

*E. coli* BL21 CodonPlus(DE3)-RIL cells were transformed using PulN-pET expression vector and grown in LB medium till OD600 reached to 0.4. Gene expression was then induced with 0.1 mM isopropyl-β-D-thiogalactoside (IPTG) and growth was continued at 37° C. with shaking at 100 rpm. After 4.5 hours of induction, cells were harvested by centrifugation at 13,000 rpm for 10 minutes at 4° C. Cell pallet was washed with 50 mM Tris-Cl pH 8.0 and re-suspended in the same buffer. Harvested cells were disrupted by sonication and cell debris was removed by centrifugation at 20,000 rpm for 10 minutes at 4° C. Supernatant thus obtained was heated at 80° C. for 30 minutes to denature heat labile host cell (*E. coli*) proteins that were removed by centrifugation. Tk-PUL obtained in the supernatant was precipitated by fractional ammonium sulfate precipitation (0-20%, 20-40% and 40-60%). Precipitates obtained after 40% and 60% ammonium sulfate saturation were pooled, dialyzed and fractionated by anion exchange chromatography using Res Q-6 mL column on Fast Protein Liquid Chromatography (FPLC) system, AKTA Purifier (GE Healthcare). The column was equilibrated with 50 mM Tris-Cl pH 8.0 before loading the protein sample. Elution of the proteins bound to the column was done by a linear gradient of 0 to 1 M sodium chloride solution (prepared in 50 mM Tris-Cl pH 8.0. Fractions containing recombinant Tk-PUL were pooled and dialyzed against 50 mM Tris-Cl pH 8.0

Enzyme Activity Assay

Pullulanase activity of recombinant Tk-PUL was measured in terms of the amount of reducing sugars librated upon incubation of the enzyme with pullulan. Maltose was used as a standard for reducing sugars. In a standard assay mixture, 125 μL of 0.5% (w/v) pullulan in 50 mM sodium citrate buffer (pH 4.2) were mixed with 125 μL of properly diluted (0.8-1.2 U/mL) enzyme (in the same buffer) and incubated at 90° C. for 10 minutes. The reaction was stopped by quenching in ice water and reducing ends released were determined by dinitrosalicylic acid (DNS) method (Bernfeld, 1955). Reducing groups released by the non-enzymatic factors were corrected by preparing enzyme blank sample (assay mixture without enzyme) and substrate blank sample (assay mixture without substrate). One unit for pullulanase activity was defined as the amount of enzyme that released 1 μmole of reducing sugars (in terms of maltose) in one minute under standard assay conditions. Protein concentration was estimated by Coomassie dye-binding assay (Bradford, 1976) using Quick Start™ Bradford Protein assay kit (Bio-Rad Laboratories, Inc., CA, USA). Bovine serum albumin was used as a standard for protein quantification. α-amylase activity of recombinant Tk-PUL was measured by the same procedure but replacing pullulan with 1% (w/v) starch as substrate.

Effect of Ph and Temperature on the Enzyme Activity

Effect of pH and temperature on pullulanase and α-amylase activities of recombinant Tk-PUL was studied using purified enzyme and same assay procedure (Bernfeld, 1955). For pH study buffers used were, 50 mM sodium citrate (pH 2.5-4.5), 50 mM sodium acetate (pH 3.25-6.5) and 50 mM sodium phosphate (pH 6.5-8.5). pH was adjusted at room temperature. To measure the effect of temperature on the enzymatic activity, assay mixtures were prepared either in 50 mM sodium citrate buffer (pH 4.2) or in 50 mM sodium acetate pH 6.5 and incubated for 10 minutes at temperatures from 40 to 120° C. An oil bath was used for temperatures above 90° C. and incubations were performed in tightly screw capped Hungate tubes to prevent boiling of the samples.

Ph Stability of Recombinant Tk-Pul

The pH stability of recombinant Tk-PUL was studied at 4° C. in buffers of various pHs (50 mM sodium citrate pH 4.2; 50 mM sodium acetate pH 6.5 and 50 mM Tris-Cl pH 8.5). The purified recombinant enzyme was diluted (0.04 mg/mL final concentration) in respective buffer and incubated at 4° C. for 56 hours. Aliquots were withdrawn at regular intervals (8 hourly) and the pH stability was studied by measuring residual pullulanase activity (in terms of reducing sugars released as maltose) using DNS method (Bernfeld, 1955).

Thermostability of Recombinant Tk-Pul

For thermostability analysis the purified enzyme was diluted (40 μg/mL final concentration) in 50 mM buffers of various pH values (sodium citrate pH 4.2, sodium acetate pH 6.5 and Tris-Cl pH 8.5) and incubated at 90° C. and 100° C. All incubations were performed in tightly screw capped Hungate tubes to prevent boiling of the samples. At various interval of time, samples (50 μL~2 μs protein) were taken, centrifuged for clarification and tested for residual pullulanase activity by standard assay method (Bernfeld, 1955).

Effect of Metal Ions on Recombinant Tk-PUL

For this study purified recombinant Tk-PUL was extensively dialyzed against 10 mM EDTA in 50 mM Tris-Cl pH 8.0. Properly diluted enzyme (1.7 U/mL, final concentration) was mixed with metal ions (either 50 μM or 5 mM, final concentrations) and incubated at 60° C. for 15 minutes. Samples were withdrawn and pullulanase activity was examined by routine assay method (Bernfeld, 1955).

Substrate Specificity and Characterization of the Hydrolysis Products

Substrate preference and relative hydrolysis rates of various polysaccharides (pullulan, starch, glycogen, amylose, amylopectin, dextrin, and cyclodextrins) were determined by incubating each of them (at a final concentration of 0.25% w/v) with recombinant Tk-PUL. Substrate solutions were prepared in 50 mM sodium citrate buffer (pH 4.2) and after adding purified enzyme (0.15 U≈2.2 μs protein) incubated at 90° C. for 2 to 30 minutes. The hydrolysis rate (μ moles of reducing sugars (maltose)/min·mL) of these substrates was measured after every 2 minutes by DNS method (Bernfeld, 1955). For characterization of oligosaccharides (obtained in hydrolysis products) incubations were done under similar conditions for up to 16 hours. The products were analyzed by High Performance Liquid Chromatography (HPLC) on Aminex HPX-42A column (Bio-Rad, USA) at 85° C. Peaks of chromatography were detected by differential refractive index detector (S 3580) on HPLC system (Sykam GmbH, Germany).

Application of Recombinant Tk-PUL in the Production of Maltose and Glucose Syrups For production of maltose syrup corn starch was suspended in 0.1 M sodium citrate buffer according to desired concentration (1%, 12% or 30% w/v). After addition of recombinant Tk-PUL the pH was adjusted to 4.2 or to the desired value. The slurry was heated at 100° C. (boiling water) for 5-10 minutes and then shifted to water bath at 90° C. for simultaneous liquefaction and saccharification. Commercial α-amylase from *B. licheniformis*; Termamyl 120 L (Sigma) was used as control for starch liquefaction under similar conditions. Samples were taken at specified intervals and oligosaccharide profile was analyzed by HPLC on Aminex HPX-42A column.

For the production of glucose syrup saccharification of liquefied starch was done by cooling it to 60° C. (after 2 hours incubation with recombinant Tk-PUL at 90° C.), adding 1.29 U of commercial glucoamylase from *Aspergillus niger* per gram of starch; AMG 300L (Sigma) and continuing incubation at 60° C. for up to 96 hours. Before addition of glucoamylase the pH (6.5) of starch liquefied by Termamyl 120L was lowered to 4.5. Analysis of degree of saccharification over time was performed by HPLC on Aminex HPX-42A column.

Results

Nucleotide and Protein Sequences

Nucleotide sequence of the cloned gene was determined by using Beckman Coulter CEQ™ 8000 Genetic Analysis System. The sequence thus obtained was in accordance with the gene sequence SEQ ID NO 1 (available at sequence databases) of *T. kodakaraenis* pullulananse. The full length gene consisted of 2298 nucleotides encoding a protein of 765 amino acids (SEQ ID NO 2). A signal peptide of 17 amino acids (shown as double underlined in FIG. 2) was predicted using SignalP 3.0 software (Bendtsen et al., 2004) and was excluded during primer designing for PCR amplification.

Sequence Analysis of Tk-PUL

Multiple sequence alignment (FIG. 3) revealed that the amino acid sequence of Tk-PUL has only 62% or less identity with already known sequences of amylolytic enzymes. Maximum identity (62%) was observed with already characterized pullulan hydrolase III from *T. aggregans* (Table 1). Four highly conserved regions that are common in almost all amylolytic enzymes (Nakajima et al., 1986) were also identified in Tk-PUL sequence (FIG. 4). Three acid residues ($Asp^{418}$, $Asp^{601}$ and $Glu^{534}$) crucial for catalytic activity were also conserved.

TABLE 1

Percent identity between amino acid sequence of Tk-PUL and that of other amylolytic enzymes.

| Amylolytic enzyme and its source | Percent identity with Tk-PUL sequence | | | | | | | | | |
|---|---|---|---|---|---|---|---|---|---|---|
| | 1 | 2 | 3 | 4 | 5 | 6 | 7 | 8 | 9 | 10 |
| 1. Tk-PUL (*T. kodakaraensis*) | 100 | 62 | 38.3 | 21.7 | 21.3 | 21.3 | 21.3 | 20.2 | 20.2 | 19.5 |

TABLE 1-continued

Percent identity between amino acid sequence of
Tk-PUL and that of other amylolytic enzymes.

| Amylolytic enzyme and its source | Percent identity with Tk-PUL sequence | | | | | | | | | |
|---|---|---|---|---|---|---|---|---|---|---|
| | 1 | 2 | 3 | 4 | 5 | 6 | 7 | 8 | 9 | 10 |
| 2. Pullulan hydrolase type III (*T. aggregans*) | 100 | 41.3 | 21.8 | 20.7 | 22 | 21 | 21.2 | 20.2 | 19.8 | |
| 3. Pullulanases (*D. mucosus*) | | 100 | 24.5 | 23.7 | 25 | 24.1 | 22.2 | 22.8 | 21.6 | |
| 4. Maltogenic α-amylase (*Bacillus cidopullulyticus*) | | | 100 | 43.8 | 41.3 | 57.4 | 55.7 | 58.7 | 55.7 | |
| 5. Cyclomaltodextrin hydrolase (*T. ethanolicus*) | | | | 100 | 47.7 | 47.7 | 44.8 | 46.7 | 45.7 | |
| 6. Neopullulanase (*T. vulgaris*) | | | | | 100 | 45.9 | 42.1 | 45.1 | 43.4 | |
| 7. Neopullulanase (*B. stearothermophilus*) | | | | | | 100 | 57.7 | 69.6 | 59.5 | |
| 8. Neopullulanase (*Bacillus* sp.) | | | | | | | 100 | 60.5 | 58.6 | |
| 9. Maltogenic amylase (*G. stearothermophilus*) | | | | | | | | 100 | 64 | |
| 10. Neopullulanase (*B. cereus*) | | | | | | | | | 100 | |

Swiss-prot accession numbers of sequences used were, 1, Q5JID9; 2, Q9P9A0; 3, Q9HHB0; 4, P32818; 5, P29964; 6, Q08751; 7, P38940; 8, Q57482; 9, Q45490; 10, Q819G8.

Purification of Recombinant Tk-PUL

Recombinant Tk-PUL was purified to apparent homogeneity on SDS-PAGE. The purified pullulanase after Resource Q column showed 11.19-fold higher specific activity (70.5 U/mg) than that of crude extract (total cell lysate having specific activity 6.3 U/mg). Overall yield after purification was 89.2%.

pH Optimum for the Enzyme Activity

Figure 5A:
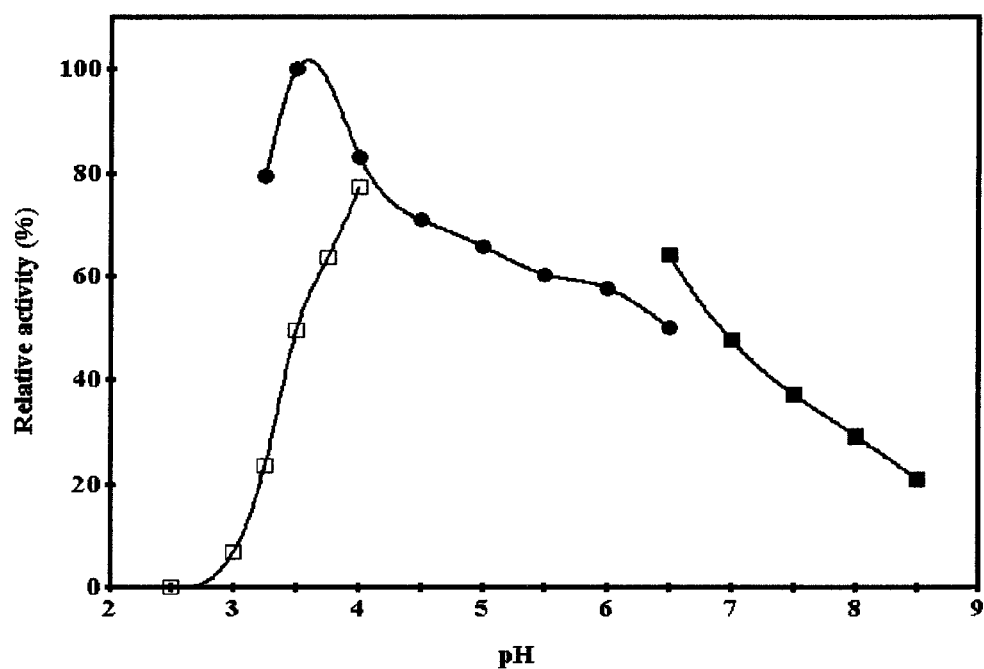
FIG. 5*a*: Graphical presentation of pullulanase activity possessed by recombinant Tk-PUL at various pH values in sodium citrate (□), sodium acetate (●) and sodium phosphate (■) buffers. Each buffer was used at a concentration of 50 mM.
Figure 5B:
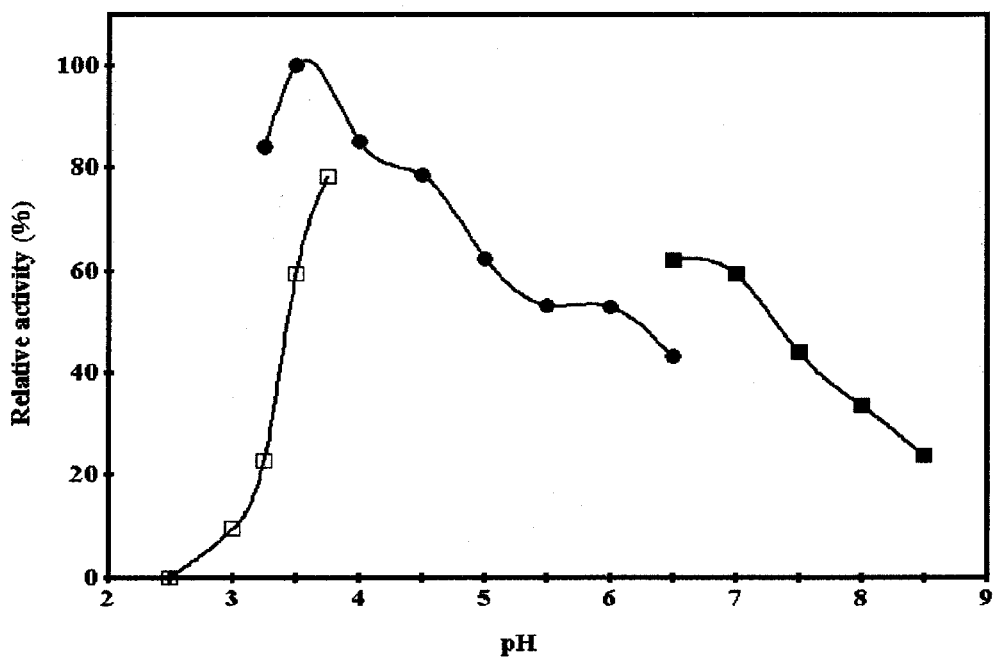
FIG. 5*b*: Graphical presentation of α-amylase activity possessed by recombinant Tk-PUL at various pH values in sodium citrate (□), sodium actetate (●) and sodium phosphate (■) buffers. Each buffer was used at a concentration of 50 mM.

The highest activities (pullulanse and α-amylase) were observed at pH 3.5 (in acetate buffer, FIG. 5*a* and FIG. 5*b*) while in citrate buffer maximum activities were observed at pH 4.25.

pH Stability of Tk-PUL

Figure 6:
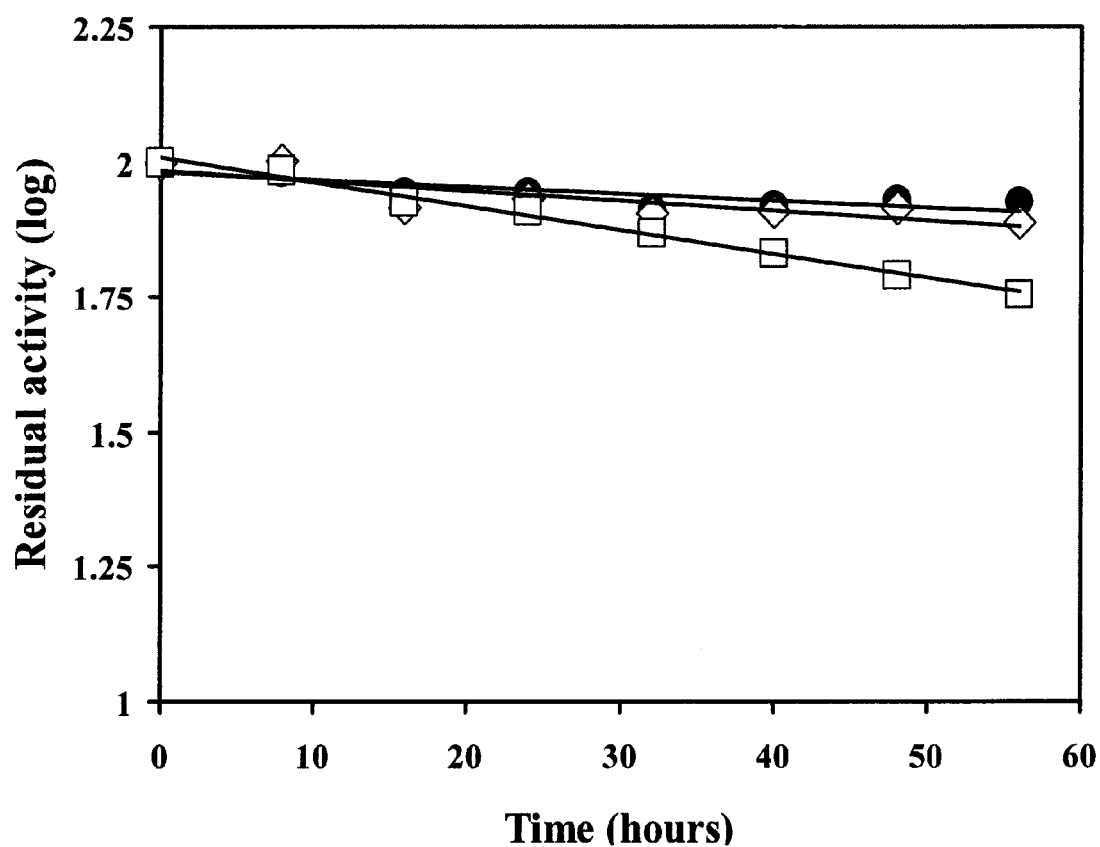
FIG. 6: Graph representing the stability of recombinant Tk-PUL at various pH values over various intervals of time. Buffers used were 50 mM sodium citrate pH 4.2 (□), 50 mM sodium acetate pH 6.5 (◇) and 50 mM Tris-Cl pH 8.5(●).

The recombinant Tk-PUL displayed 84.47%, 77.47% and 56.86% of the maximal activities after 56 hour incubation (at 4° C.) at pH values 8.5, 6.5, and 4.2, respectively (FIG. 6). These results indicated that the enzyme is more stable in alkaline pH though it has highest activity in acidic pH.

Optimum Temperature for Activity of Recombinant Tk-PUL

Figure 7:
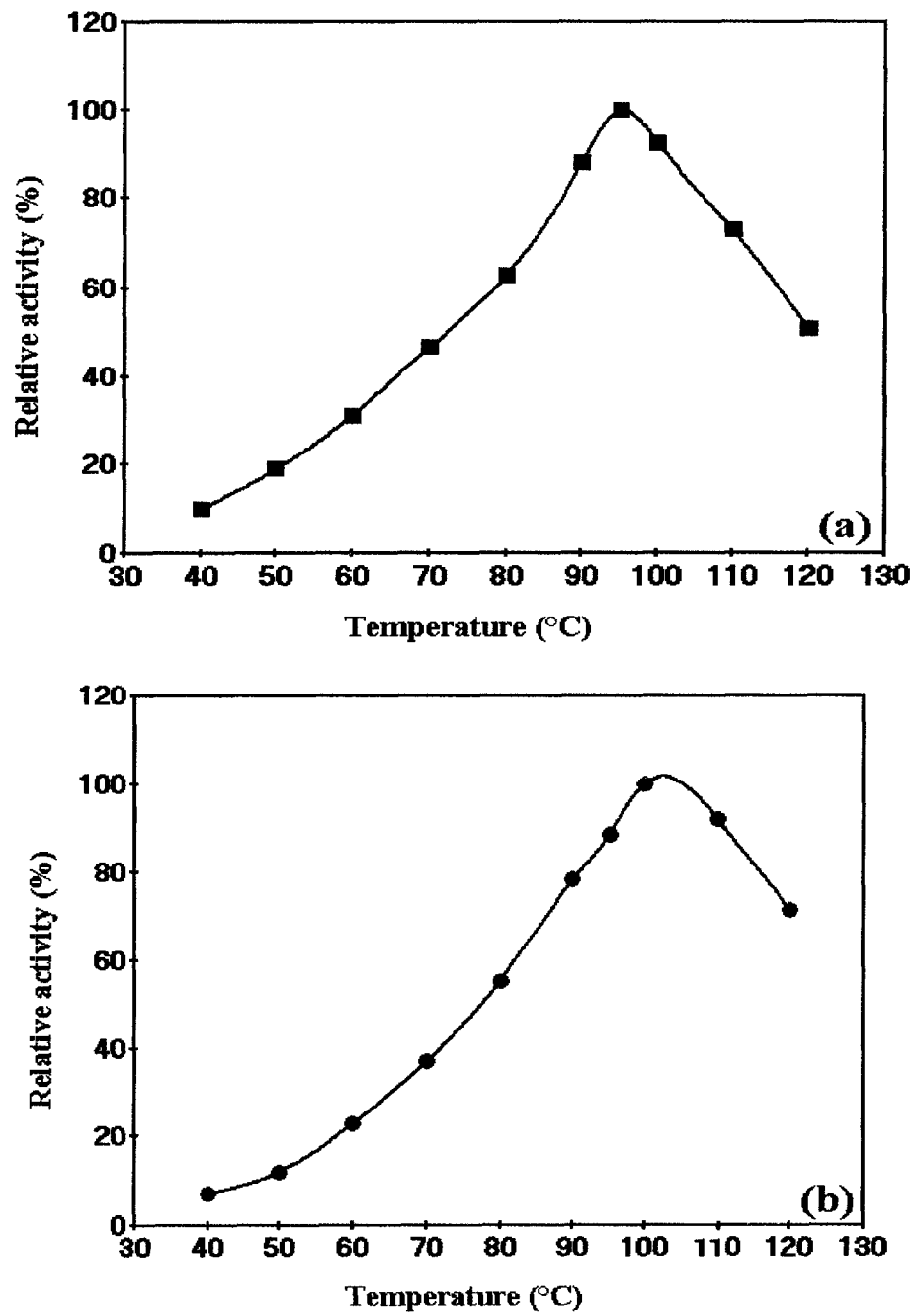
FIG. 7: Graph representing relative pullulanase activity at various temperatures. (a) Activity in sodium citrate buffer pH 4.2. (b) Activity in sodium acetate buffer pH 6.5.
Figure 8:
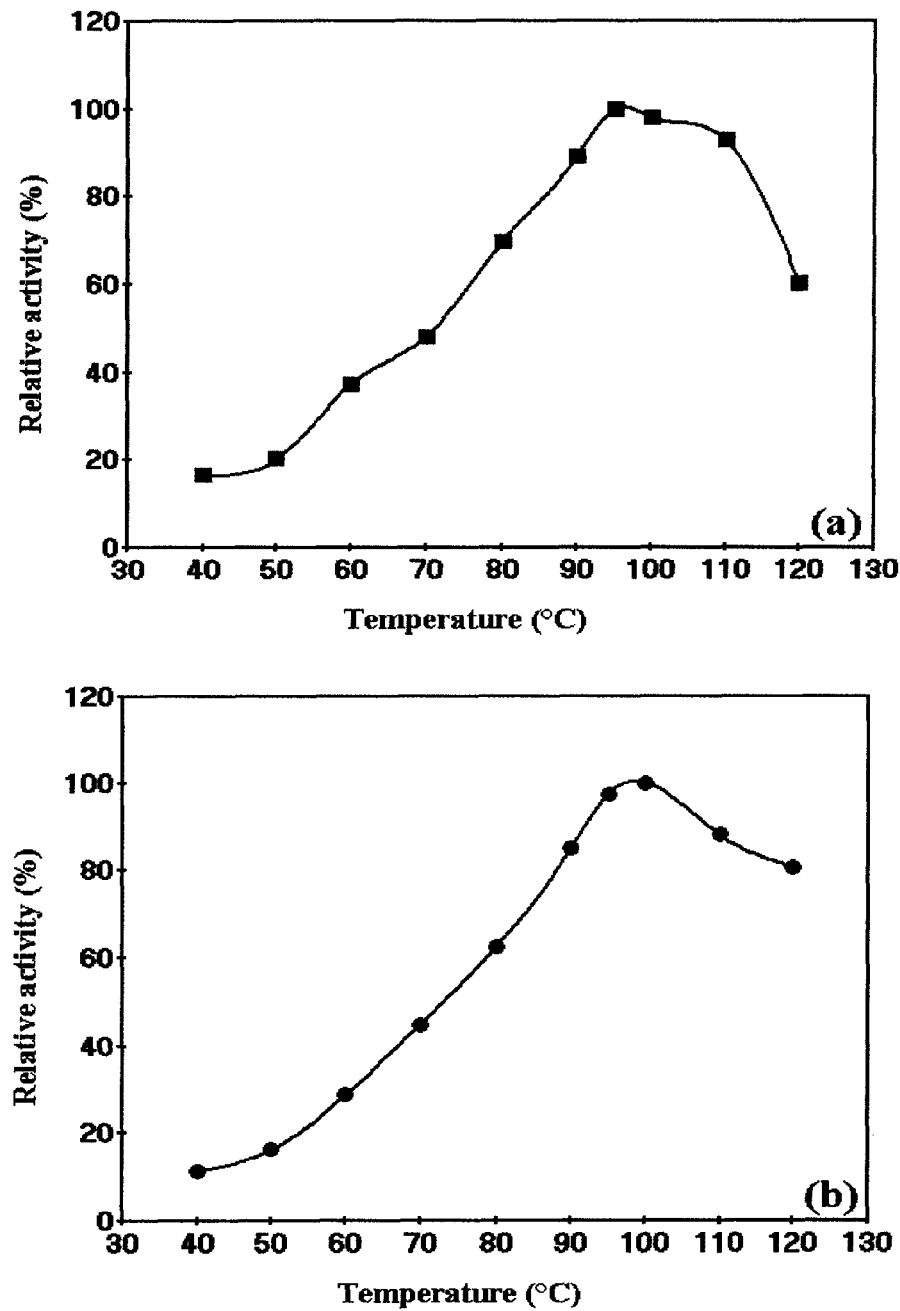
FIG. 8: Graph representing the relative α-amylase activity at various temperatures. (a) Activity in sodium citrate buffer pH 4.2. (b) Activity in sodium acetate buffer pH 6.5.

The maximal pullulanase and α-amylase activities of recombinant Tk-PUL were observed at 100° C. in case of acetate buffer (pH 6.5) while in case of citrate buffer (pH 4.2) the maximal activities were observed at 95° C. Even at 120° C. the enzyme displayed more than 50% of the maximal activities (FIGS. 7 and 8).

Effect of Metal Ions on the Activity of Recombinant Tk-PUL

No increase in activity of Tk-PUL was observed in the presence of calcium (0-5 mM, final concentration in assay mixture) which indicated that unlike other amylolytic enzymes, recombinant Tk-PUL does not depend on calcium for its activity (Table 2). The activity of Tk-PUL was also not affected by the presence of $Mg^{+2}$, $Mn^{+2}$, $Co^{+2}$ and $Zn^{+2}$ while $Ni^{+2}$, $Cu^{+2}$ and $Fe^{+2}$ had inhibitory effect at 5 mM concentration but no effect at 0.05 mM concentration as shown in Table 3.

TABLE 2

Pullulanase activity in the presence and absence of calcium.

| [$CaCl_2$] (mM) | Relative activity (%) |
|---|---|
| 0.00 | 100.00 |
| 0.02 | 104.12 |
| 0.05 | 104.47 |
| 0.10 | 97.92 |
| 0.50 | 103.76 |
| 1.00 | 104.12 |
| 5.00 | 97.74 |

Purified recombinant Tk-PUL was extensively dialyzed against 10 mM EDTA in 50 mM Tris-Cl pH 8.0. Properly diluted enzyme (1.7 U/mL, final concentration) was mixed with various concentrations of calcium chloride and incubated at 60° C. for 15 minutes. Samples were withdrawn and pullulanase activity was examined by DNS method (Bernfeld, 1955).

TABLE 3

Pullulanase activity in the presence of various concentrations of metal ions.

| | Metal ion concentration (mM) | | |
|---|---|---|---|
| | 0 | 0.050 | 5 |
| Metal ion used | Relative activity (%) | | |
| $Mg^{+2}$ | 100 | 98.5 | 95 |
| $Mn^{+2}$ | 100 | 102 | 104 |
| $Co^{+2}$ | 100 | 107 | 94 |
| $Zn^{+2}$ | 100 | 100 | 94 |
| $Ni^{+2}$ | 100 | 97 | 89.5 |
| $Cu^{+2}$ | 100 | 99 | 47.8 |
| $Fe^{+2}$ | 100 | 91.5 | 32.7 |
| $Ca^{+2}$ | 100 | 102 | 103 |

Purified recombinant Tk-PUL was extensively dialyzed against 10 mM EDTA in 50 mM Tris-Cl pH 8.0. Properly diluted enzyme (1.7 U/mL, final concentration) was mixed with metal ions (either 50 μM or 5 mM, final concentrations) and incubated at 60° C. for 15 minutes. Samples were withdrawn and pullulanase activity was examined by DNS method (Bernfeld, 1955).

Thermostability of Tk-PUL

Figure 9:
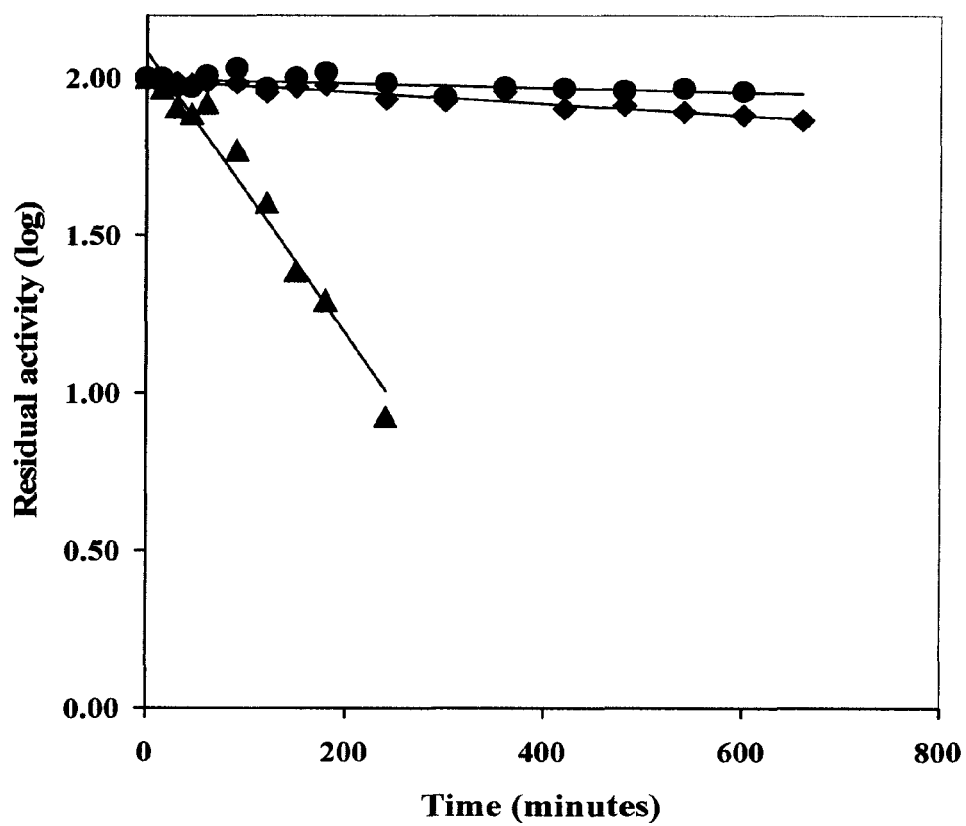
FIG. 9: Stability of Tk-PUL at 90° C. in buffers of various pH values. 50 mM buffers used were sodium citrate pH 4.2 (▲), sodium acetate pH 6.5 (●) and Tris-Cl pH 8.5 (♦).
Figure 10:
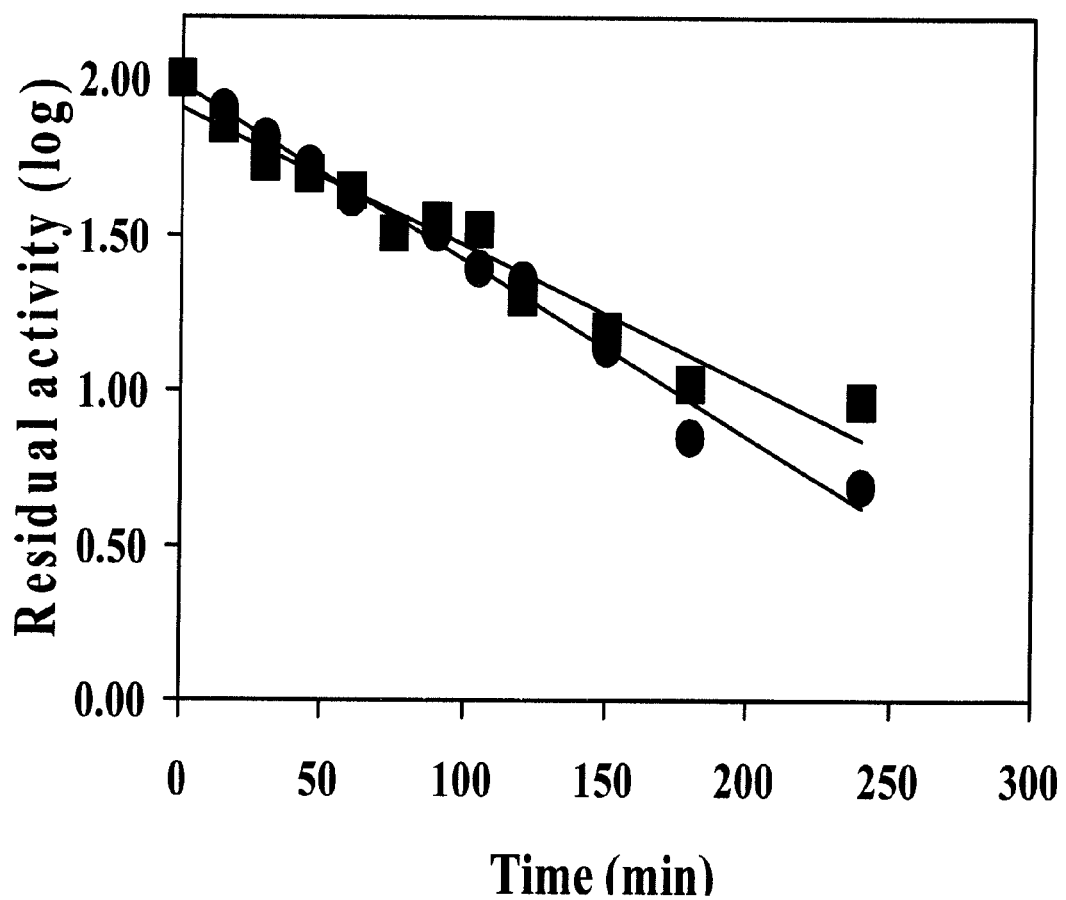
FIG. 10: Stability of Tk-PUL at 100° C. in sodium acetate pH 6.5 (■) and Tris-Cl pH 8.5 (●). Each buffer was used at a final concentration of 50 mM.

The enzyme was highly stable at 90° C. (in the absence of substrates) in buffers of pH 6.5 and pH 8.5. Almost no loss of activity was seen even after 4 hours of incubation at this temperature. After 10 hours of incubation at 90° C., 90.36% and 76.49% of the maximal activity was found at pH 6.5 and pH 8.5, respectively (FIG. 9). The half-life of Tk-PUL was 45 minutes at 100° C. (in the absence of substrates) in both buffers (FIG. 10). The half-life of Tk-PUL in pH 4.2 buffer at 90° C. (in the absence of substrates) was 100 minutes as shown in FIG. 9.

Substrate Preference and Relative Hydrolysis Rate

Besides pullulan (having 100% hydrolysis rate), the most preferred substrate by the Tk-PUL was γ-cyclodextrin. The other carbohydrates were hydrolyzed in the following preference order; γ-cyclodextrin (75.65%)>potato starch (60.13%)>amylose (45.58%)>corn starch (40.74%)>dextrin (42.68%)>amylopectin (37.02%)>glycogen (25.86%)>β-cyclodextrin (4.83%).

End products analysis on HPLC revealed that Tk-PUL was able to hydrolyze cyclodextrins (α, β and γ) which are commonly known as competitive inhibitors of pullulanases. Smaller linear oligosaccharides from maltoheptaose to maltotriose were also hydrolyzed but at a slower rate. Final products of hydrolysis (from long chain and small chain saccharides) comprised of a mixture of maltotriose, maltose and glucose with predominant concentrations of maltose. It is worth mentioning that recombinant Tk-PUL was also able to hydrolyze maltotriose into maltose and glucose. Pullulan was hydrolyzed to a mixture of maltotriose, maltose, panose and isomaltose indicating that the enzyme hydrolyzes α-1,4 glycosidic linkages in pullulan in addition to α-1,6 linkages. On the basis of this fact Tk-PUL is proposed as pullulan hydrolase type III though it was previously annotated as pullulanase type II in the genome of *T. kodakaraensis*.

Recombinant Tk-PUL hydrolyzes the pullulan so efficiently that within 10 minutes more than 98% pullulan was converted to trisaccharides (maltotriose/panose) in the presence of 2.6 U≈40 μg of the enzyme when 0.25% w/v pullulan (final concentration) was used. To our knowledge none of the previously reported enzymes could hydrolyze the pullulan so efficiently. Data regarding the amount of enzyme utilized in the end product analysis experiments are also missing in previous reports. Recombinant Tk-PUL was also able to subsequently hydrolyze maltotriose into maltose and glucose. This unique feature of hydrolyzing trisaccharide maltotriose to maltose and glucose was also not reported previously.

Application of Tk-PUL in the Production of Maltose Syrup from Corn Starch

Time Course Hydrolysis of Corn Starch

Figure 11:
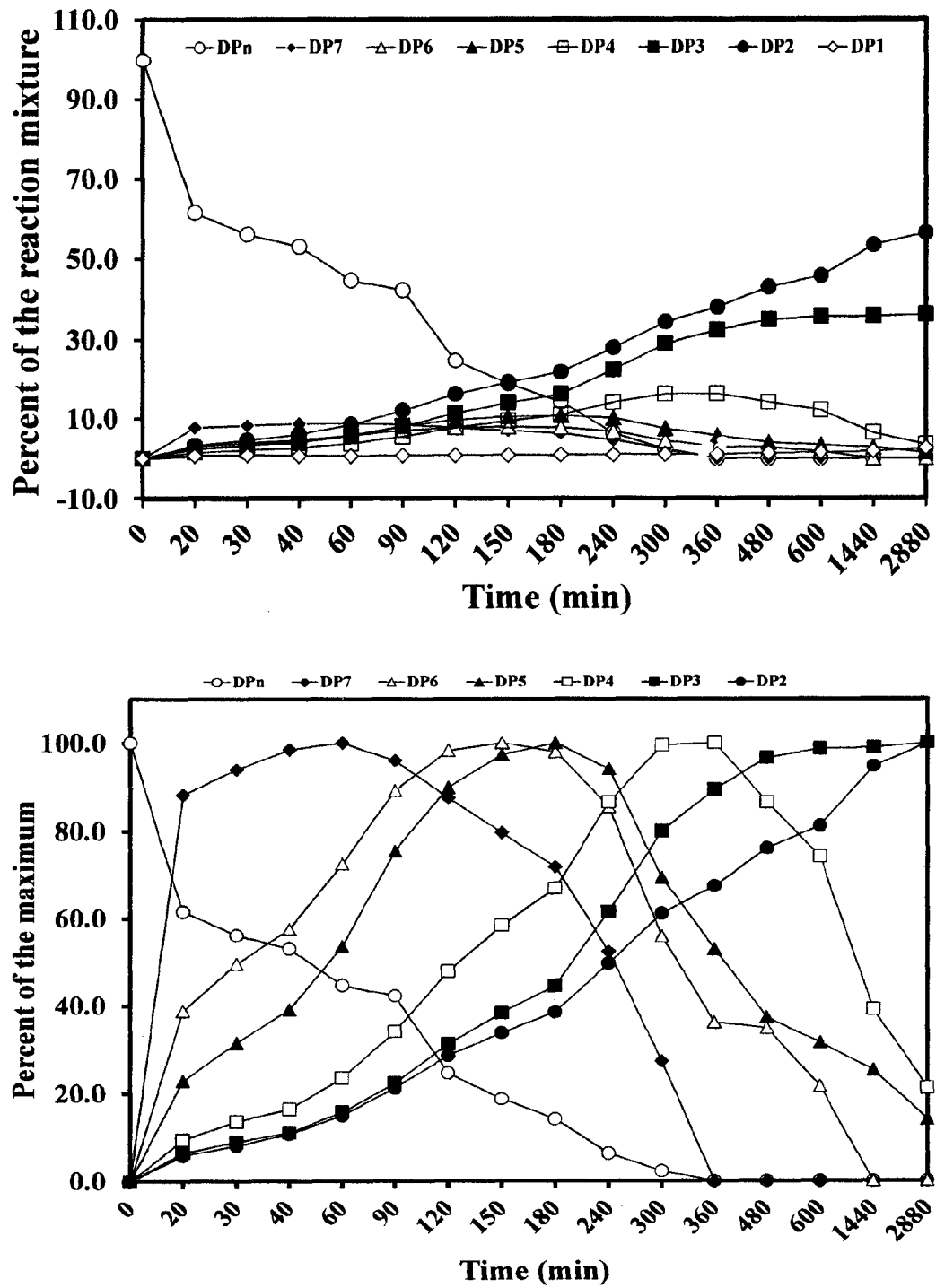
FIG. 11: Time course release of oligosaccharides from 1% (w/v) corn starch by the action of recombinant Tk-PUL. Upper panel represents sugars released as percentage of the total products against hydrolysis time. Lower panel shows sugars as percent of their maximum (released) against hydrolysis time. DP stands for degree of polymerization while DP7 to DP1 are representing maltoheptaose to glucose, respectively.

In order to analyze the suitability of Tk-PUL in the production of glucose and maltose syrups time course hydrolysis of corn starch was performed. Purified Tk-PUL (1.6 mg of protein per gram of starch on dry basis) was incubated with 1% (w/v) starch (final concentration) in 0.1M sodium citrate buffer pH 4.2 at 90° C. At regular intervals samples were taken and saccharide composition was analyzed by HPLC on Aminex HPX-42A column. Starch was completely hydrolyzed to maltohexaose and smaller oligosaccharides within 6 hours and after 48 hours of incubation maltose concentration of the reaction mixture reached to 56% as represented in Table 4 and FIG. 11. These results indicated that Tk-PUL can be a candidate for application in starch industry for the production of maltose syrup even in the absence of α-amylase (required for liquefaction of starch) and β-amylase (maltogenic enzyme for saccharification).

Production of Maltose Syrup from 12% Starch

Purified Tk-PUL (0.67 mg/g starch on dry basis) was added to 12% (w/v) starch slurry (final concentration in 0.1 M sodium citrate buffer pH 4.2) and incubated first at 100° C. for 10 minutes and then at 90° C. for up to 72 hours. Saccharide composition was analyzed at regular intervals on Aminex HPX-42A column. After 72 hours of incubation maltose was the predominant sugar (26.2%) and more than 58% of the hydrolysates were oligosaccharides from DP4-DP1 (Table 5).

TABLE 5

Production of maltose syrup from 12% (w/v) corn starch.

| Time | Products concentration (%) | | | | | | | | |
|---|---|---|---|---|---|---|---|---|---|
| (Min) | DPn | DP7+ | DP7 | DP6 | DP5 | DP4 | DP3 | DP2 | DP1 |
| 0 | 100 | 0 | 0 | 0 | 0 | 0 | 0 | 0 | 0 |
| 2 | 81.6 | 0 | 7.0 | 0 | 1.8 | 1.3 | 3.0 | 5.3 | 0 |
| 3 | 77.8 | 0 | 5.6 | 2.2 | 2.3 | 1.7 | 3.6 | 6.3 | 0.5 |
| 5 | 71.2 | 1.7 | 5.6 | 2.8 | 3.0 | 2.6 | 4.8 | 8.1 | 0.2 |
| 48 | 24.4 | 7.0 | 3.5 | 5.2 | 7.3 | 9.4 | 18.2 | 23.7 | 1.3 |
| 72 | 16.8 | 7.7 | 3.7 | 5.5 | 7.9 | 10.2 | 19.8 | 26.4 | 2.0 |

Purified Tk-PUL (0.67 mg/g starch on dry basis) was added to 12% (w/v) starch slurry (final concentration in 0.1M sodium citrate buffer pH 4.2) and incubated first at 100° C. for 10 minutes and then at 90° C. for upto 72 hours. Saccharide composition was analyzed at regular intervals on Aminex HPX-42A column.
DP stands for degree of polymerization while DP7 to DP1 are representing maltoheptaose to glucose, respectively.

Production of Maltose Syrup from 30% Starch

Purified Tk-PUL (1 mg/g starch on dry basis) was incubated with 30% (w/v) starch under similar conditions as described above and saccharide composition was similarly analyzed by HPLC on Aminex HPX-42A column. More than 50% of the hydrolysis products were consisting of DP1-DP3 with major proportion of maltose (25.4%) as analyzed after 96 hours of incubation (as shown in Table 6).

TABLE 6

Production of maltose syrup from 30% (w/v) corn starch.

| Time | Products concentration (%) | | | | | | | | |
|---|---|---|---|---|---|---|---|---|---|
| (Hrs.) | DPn | DP7+ | DP7 | DP6 | DP5 | DP4 | DP3 | DP2 | DP1 |
| 0 | 100 | 0 | 0 | 0 | 0 | 0 | 0 | 0 | 0 |
| 2 | 79.1 | 2.3 | 3.2 | 2.3 | 2.1 | 1.8 | 3.6 | 5.6 | 0 |
| 3 | 77.4 | 2.2 | 3 | 2.3 | 2.2 | 2.1 | 4 | 6.5 | 0.3 |
| 8 | 54.3 | 6.2 | 4.3 | 4.5 | 4.7 | 4.9 | 8.4 | 12.2 | 0.5 |
| 10 | 49.2 | 6.6 | 4.6 | 5 | 5.3 | 5.7 | 9.5 | 13.6 | 0.5 |
| 48 | 11.4 | 10.8 | 4.5 | 6.4 | 9.5 | 11.1 | 20.5 | 24.6 | 1.2 |
| 96 | 11.2 | 8.3 | 4 | 5.7 | 9.4 | 11.1 | 21.6 | 25.4 | 3.3 |

Purified Tk-PUL (1 mg/g starch on dry basis) was added to 30% (w/v) starch slurry (final concentration in 0.1M sodium citrate buffer pH 4.2) and incubated first at 100° C. for 10 minutes and then at 90° C. for upto 96 hours. Saccharide composition was analyzed at regular intervals on Aminex HPX-42A column.
DP stands for degree of polymerization while DP7 to DP1 are representing maltoheptaose to glucose, respectively.

Application of Tk-PUL in the Production Glucose Syrup

Liquefaction of Corn Starch

Figure 12A:
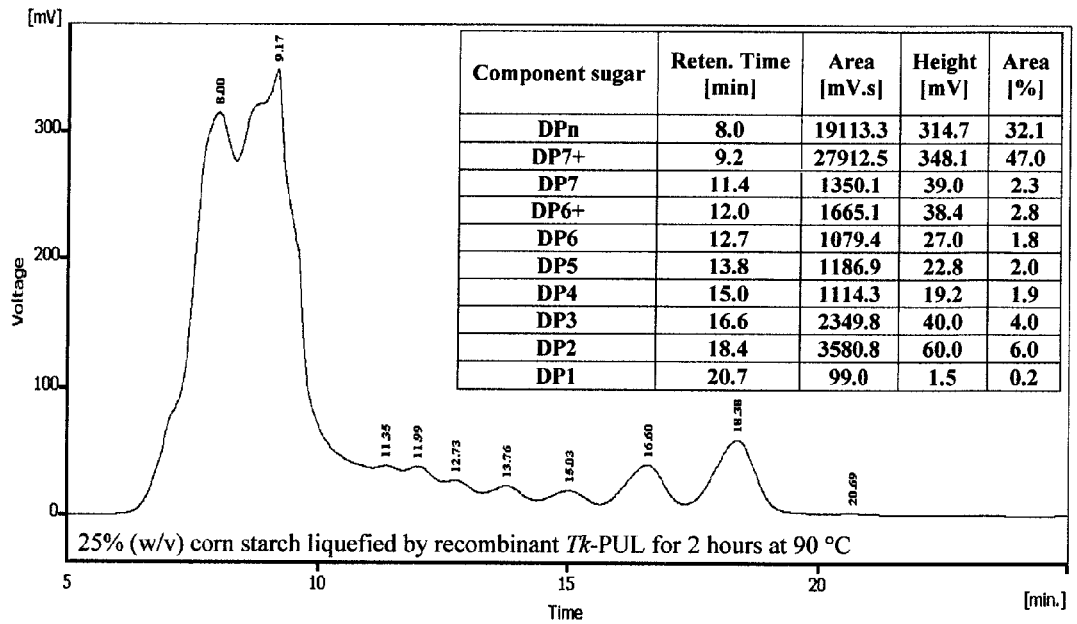
FIG. 12a: HPLC profile showing liquefaction of 25% (w/v) corn starch by the action of recombinant Tk-PUL.
Figure 12B:
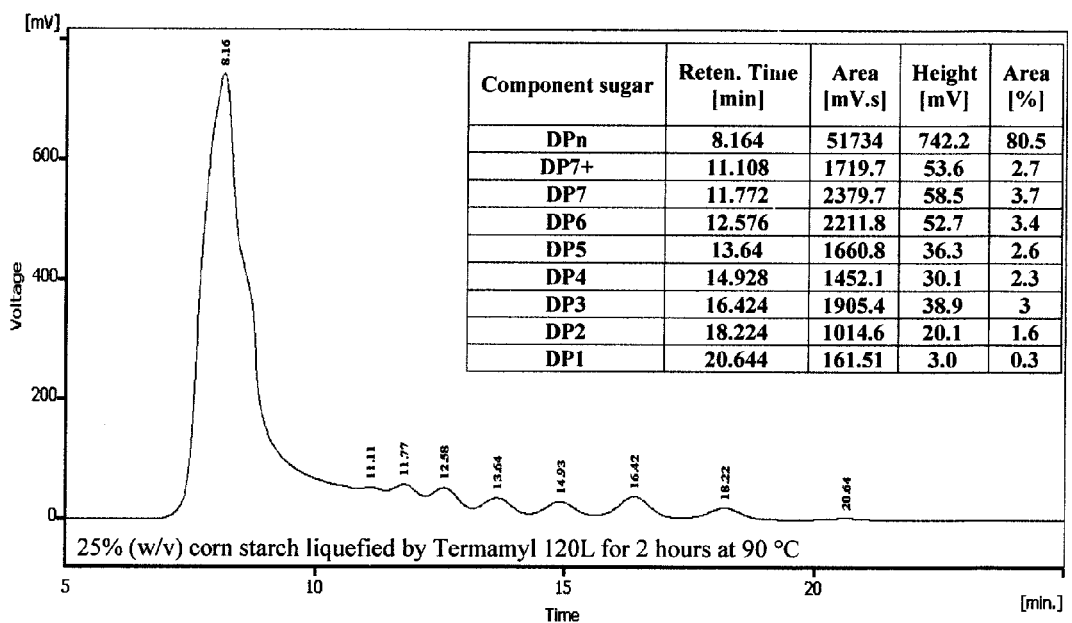
FIG. 12b: HPLC profile showing liquefaction of 25% (w/v) corn starch by the action of α-amylase from *B. licheniformis*; Termamyl 120L.

For liquefaction of corn starch commercial α-amylase from *B. licheniformis*; Termamyl 120L was used as control. Tk-PUL and control enzyme (equivalent to 70 pullulanase U/g dry starch) were added into 25% (w/v) starch slurry. Calcium at a final concentration of 2 mM was additionally added in control experiment (containing Termamyl 120L) but not in Tk-PUL containing experiment. pH of the slurry in control was adjusted to 6.0 while for Tk-PUL it was adjusted to 4.2. Both the mixtures were incubated at 100° C. for 10 minutes and then at 90° C. HPLC analysis of hydrolysis products after 2 hours of incubation revealed that oligosaccharide profile obtained by the action of Tk-PUL was different from that obtained by the action of commercial enzyme (Termamyl 120L). Maltotriose and maltose (DP3 and DP2) were the predominant saccharides among low molecular weight products obtained by the action of Tk-PUL (after 2 hours) while non-significant amounts of these sugars were observed in the starch hydrolyzed by the action of Termamyl 120L (FIG. 12a and FIG. 12b).

Saccharification of Liquefied Corn Starch

Figure 13A:
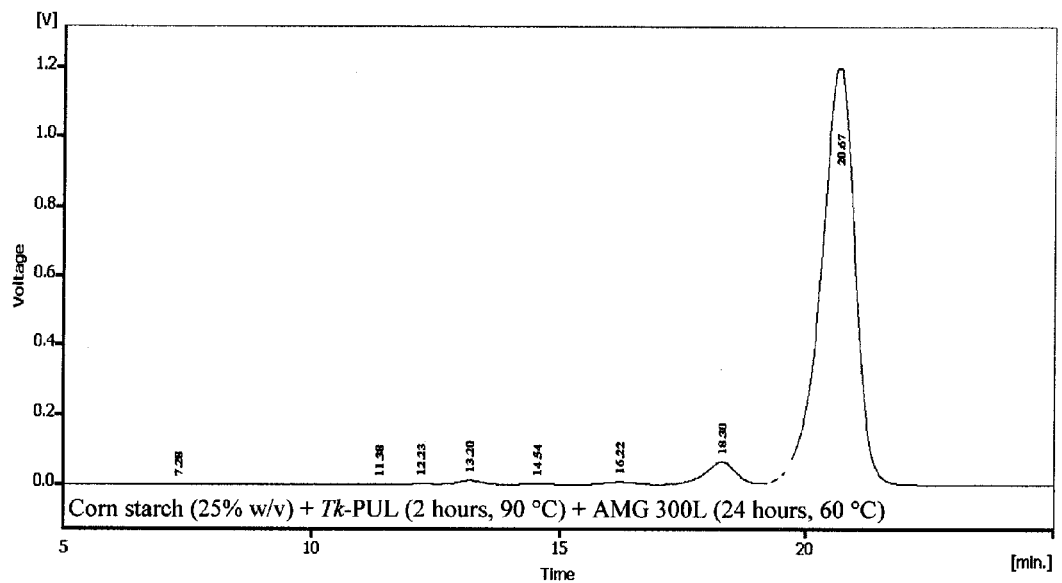
FIG. 13a: HPLC profile showing final saccharide composition of glucose syrup produced from corn starch liquefied by the action of recombinant Tk-PUL. The highest peak with retention time 20.7 minutes is representing glucose.
Figure 13B:
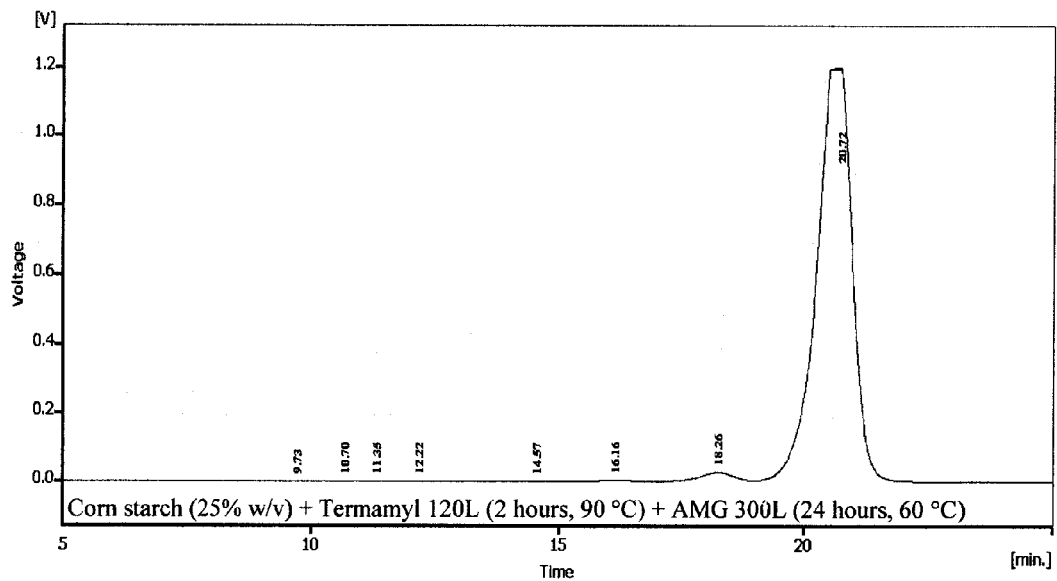
FIG. 13b: HPLC profile showing final saccharide composition of glucose syrup produced from corn starch liquefied by the action of α-amylase from *B. licheniformis*; Termamyl 120L. The highest peak with retention time 20.7 minutes is representing glucose

For saccharification the liquefied starch was cooled to 60° C. and commercial glucoamylase from *Aspergillus niger*; AMG 300L was added (1.29 U/g starch). pH of the starch liquefied by Termamyl 120L was lowered to 4.5 while starch liquefied with Tk-PUL required no pH adjustment (already at 4.2). Both the mixtures were then incubated at 60° C. for further 24 hours. Final saccharide composition in Tk-PUL treated sample (liquefied starch) was significantly similar to that observed in the sample treated with commercial α-amylase from *B. licheniformis*. These results are shown in Table 7, FIG. 13a and FIG. 13b.

TABLE 7

Saccharide composition of glucose syrup produced by the action of recombinant Tk-PUL and commercial α-amylase from *B. licheniformis*.

| Liquefying Enzyme used | DP1 | DP2 | DP3 | DP4+ |
|---|---|---|---|---|
| Termamyl 120L (α-amylase from *B. licheniformis*) | 96.7 | 2.2 | 0.3 | 0.8 |
| Tk-PUL | 92.9 | 4.9 | 0.8 | 1.4 |

25% (w/v) starch slurry was liquefied either by Termamyl 120L (at pH 6.0 in the presence of 2 mM calcium) or by Tk-PUL (at pH 4.2 in the absence of calcium) at 100° C. for 10 minutes and then at 90° C. for 2 hours. Saccharification was performed by commercial glucoamylase from *Aspergillus niger*; AMG 300L at 60° C. DP1, DP2 and DP3 represent glucose, maltose and maltotriose, respectively.

The invention claimed is:

1. A process consisting of simultaneous liquefaction and saccharification of starch consisting of:
    a. adding a pullulan hydrolase consisting of an amino acid sequence of SEQ ID NO:2 to a starch solution,
    b. heating the starch solution to about 100° C. and maintaining the starch solution at this temperature for 10 minutes;
    c. cooling the starch solution to 90° C. and maintaining the starch solution at this temperature for six hours.

2. The process according to claim 1, wherein the pH is maintained at 4.2 throughout the process.

3. The process according to claim 1, wherein both liquefaction and saccharification are carried out without the addition of calcium or any other metal ions.

4. A process consisting of liquefaction of a starch solution in the presence of a pullulan hydrolase consisting of amino acid sequence of SEQ ID NO:2 at a pH of about 4.2 in the absence of calcium followed by saccharification of the liquefied starch by *Aspergillus niger* glucoamylase without pH adjustment.

5. The process according to claim 1, wherein a mixture of maltotriose, maltose, and glucose are produced.

* * * * *

SEQUENCE LISTING

<160> NUMBER OF SEQ ID NOS: 4

<210> SEQ ID NO 1
<211> LENGTH: 2298
<212> TYPE: DNA
<213> ORGANISM: Thermococcus kodakaraensis

<400> SEQUENCE: 1

```
atgaaaaaag gtggtctgct gctcattctc ctgattctgg tctcaatcgc cagcggatgt      60
atctcggaga gcaacgaaaa tcaaactgca acggcttcga ccgttccacc gacttcagtg     120
acaccctcac agtcttccac tcccacaacc tcgacctcga cgtacggccc ttccgaaaga     180
acggagctta aacttccttc ggttaactac actcccatct acgtcggcat agagaaaggc     240
tgtccctccg gaagagtccc ggtgaagttc acgtacaacc ccggaaacaa gaccgtaaag     300
tctgtcagcc tccgcgggag cttcaacaac tggggagagt ggccgatgga gctgaagaac     360
ggcacgtggg agacgaccgt ctgtctccgc cctggaaggt atgagtataa gtacttcatc     420
aacggccagt gggtcaagga catgtccgac gacgggacgg gaaggcccta cgaccccgat     480
gcagacgcct atgcccccga tggctacggg ggaaagaacg ccgtgagggt agttgagggc     540
cgcgaagcgt tctacgtgga gttcgatcca agagacccag cctacctcag catcgcggac     600
aaaagaaccg tggtcaggtt cgaggctaag agagacaccg tcgagtctgc ggttctcgtt     660
acggatcacg ggaactacac gatgaagctt caggtctggt gggacttcgg cgaaacctgg     720
cgcgccgaga tgccagttga acccgctgat tattacattc tcgtaacctc ctccgacggc     780
gggaagtttg ccgtcctaaa cacaagcgaa agcccgttct tccactttga tggcgttgag     840 gggttcccc agctggagtg ggtgagcaac gggataacct accagatatt ccccgacagg     900
ttcaacaacg gcaataaaag caacgatgcc ctagctttgg atcacgacga gctaattttg     960
aaccaggtta atccagggca gccaatcctc tccaactgga gcgacccgat aacgcccctc    1020
cactgctgcc accagtactt cggcggcgac ataaagggaa taacggagaa gctcgactac    1080
cttcagagcc taggtgttac tataatctac atcaacccga ttttcctctc gggaagcgcc    1140
cacggctacg acacctacga ctactaccgg ctcgacccca agttcgggac cgaggatgag    1200
ctgagagagt tcctcgatga ggcccacagg aggggaatga gggtaatctt cgatttcgtg    1260
cccaaccact gcggcatagg gaatccagcc ttcctcgacg tctgggagaa gggcaacgaa    1320
agcccatact gggactggtt cttcgtcaag aagtggccct tcaagctcgg cgatgggagc    1380
```

```
gcctacgtcg gctggtgggg ctttgggagc cttccgaagc tcaacactgc caaccaggag    1440
gtcagggagt acctgatagg agcggccctc cactggatag agttcggctt tgacggcatt    1500
agggtggatg tgccgaacga agtcctcgac ccggggacgt tcttcccgga gctgagaaag    1560
gcagttaagg agaaaaagcc cgacgcgtac ctcgtcggcg agatatggac gctctccccg    1620
gagtgggtga agggagaccg cttcgactcc ctcatgaact acgccctcgg gagggacatc    1680
ctcctgaact acgctaaggg cctgctcagc ggagaaagtg caatgaaaat gatgggacgt    1740
tactacgctt cctacggcga gaacgtagtt gcgatgggct tcaacctcgt tgattcgcac    1800
gacacttcga ggggttctcac tgacctcggt ggtggcaaac tgggagacac accgtcaaac    1860
gagtcaattc agaggctcaa gctcctctca acgctcctct atgccctgcc cggaactccc    1920
gtcaccttcc aggggacgga gaggggactg ctcggagaca aggacactac cgatgagcaa    1980
cgctatccga tacagtggga tactgtgaac gaggacgtcc tgaaccacta cagggcactg    2040
gcggagctca gaaaaagagt tcccgcattg aggagcagcg caatgaggtt ctacactgcc    2100
aaaggcggcg ttatggcctt cttcagggga catcatgacg aggttctcgt cgttgccaac    2160
agctggaaga agccagcccct actggagctt cccgagggag agtggaaagt aatctggcct    2220
gaggatttca gcccggaact gcttcgcggc acagttgaag tgccagccat agggataatc    2280
atccttgagc ggggttga                                                  2298

<210> SEQ ID NO 2
<211> LENGTH: 765
<212> TYPE: PRT
<213> ORGANISM: Thermococcus kodakaraensis

<400> SEQUENCE: 2

Met Lys Lys Gly Gly Leu Leu Ile Leu Leu Ile Leu Val Ser Ile
1               5                   10                  15

Ala Ser Gly Cys Ile Ser Glu Ser Asn Glu Asn Gln Thr Ala Thr Ala
            20                  25                  30

Ser Thr Val Pro Pro Thr Ser Val Thr Pro Ser Gln Ser Ser Thr Pro
        35                  40                  45

Thr Thr Ser Thr Ser Thr Tyr Gly Pro Ser Glu Arg Thr Glu Leu Lys
    50                  55                  60

Leu Pro Ser Val Asn Tyr Thr Pro Ile Tyr Val Gly Ile Glu Lys Gly
65                  70                  75                  80

Cys Pro Ser Gly Arg Val Pro Val Lys Phe Thr Tyr Asn Pro Gly Asn
                85                  90                  95

Lys Thr Val Lys Ser Val Ser Leu Arg Gly Ser Phe Asn Asn Trp Gly
            100                 105                 110

Glu Trp Pro Met Glu Leu Lys Asn Gly Thr Trp Glu Thr Thr Val Cys
        115                 120                 125

Leu Arg Pro Gly Arg Tyr Glu Tyr Lys Tyr Phe Ile Asn Gly Gln Trp
    130                 135                 140

Val Lys Asp Met Ser Asp Asp Gly Thr Gly Arg Pro Tyr Asp Pro Asp
145                 150                 155                 160

Ala Asp Ala Tyr Ala Pro Asp Gly Tyr Gly Lys Asn Ala Val Arg
                165                 170                 175

Val Val Glu Gly Arg Glu Ala Phe Tyr Val Glu Phe Asp Pro Arg Asp
            180                 185                 190

Pro Ala Tyr Leu Ser Ile Ala Asp Lys Arg Thr Val Val Arg Phe Glu
        195                 200                 205
```

```
Ala Lys Arg Asp Thr Val Glu Ser Ala Val Leu Val Thr Asp His Gly
210                 215                 220
Asn Tyr Thr Met Lys Leu Gln Val Trp Trp Asp Phe Gly Glu Thr Trp
225                 230                 235                 240
Arg Ala Glu Met Pro Val Glu Pro Ala Asp Tyr Tyr Ile Leu Val Thr
                245                 250                 255
Ser Ser Asp Gly Gly Lys Phe Ala Val Leu Asn Thr Ser Glu Ser Pro
                260                 265                 270
Phe Phe His Phe Asp Gly Val Glu Gly Phe Pro Gln Leu Glu Trp Val
            275                 280                 285
Ser Asn Gly Ile Thr Tyr Gln Ile Phe Pro Asp Arg Phe Asn Asn Gly
290                 295                 300
Asn Lys Ser Asn Asp Ala Leu Ala Leu Asp His Asp Glu Leu Ile Leu
305                 310                 315                 320
Asn Gln Val Asn Pro Gly Gln Pro Ile Leu Ser Asn Trp Ser Asp Pro
                325                 330                 335
Ile Thr Pro Leu His Cys Cys His Gln Tyr Phe Gly Gly Asp Ile Lys
            340                 345                 350
Gly Ile Thr Glu Lys Leu Asp Tyr Leu Gln Ser Leu Gly Val Thr Ile
            355                 360                 365
Ile Tyr Ile Asn Pro Ile Phe Leu Ser Gly Ser Ala His Gly Tyr Asp
        370                 375                 380
Thr Tyr Asp Tyr Tyr Arg Leu Asp Pro Lys Phe Gly Thr Glu Asp Glu
385                 390                 395                 400
Leu Arg Glu Phe Leu Asp Glu Ala His Arg Arg Gly Met Arg Val Ile
                405                 410                 415
Phe Asp Phe Val Pro Asn His Cys Gly Ile Gly Asn Pro Ala Phe Leu
            420                 425                 430
Asp Val Trp Glu Lys Gly Asn Glu Ser Pro Tyr Trp Asp Trp Phe Phe
            435                 440                 445
Val Lys Lys Trp Pro Phe Lys Leu Gly Asp Gly Ser Ala Tyr Val Gly
    450                 455                 460
Trp Trp Gly Phe Gly Ser Leu Pro Lys Leu Asn Thr Ala Asn Gln Glu
465                 470                 475                 480
Val Arg Glu Tyr Leu Ile Gly Ala Ala Leu His Trp Ile Glu Phe Gly
                485                 490                 495
Phe Asp Gly Ile Arg Val Asp Val Pro Asn Glu Val Leu Asp Pro Gly
            500                 505                 510
Thr Phe Phe Pro Glu Leu Arg Lys Ala Val Lys Glu Lys Lys Pro Asp
            515                 520                 525
Ala Tyr Leu Val Gly Glu Ile Trp Thr Leu Ser Pro Glu Trp Val Lys
            530                 535                 540
Gly Asp Arg Phe Asp Ser Leu Met Asn Tyr Ala Leu Gly Arg Asp Ile
545                 550                 555                 560
Leu Leu Asn Tyr Ala Lys Gly Leu Leu Ser Gly Glu Ser Ala Met Lys
                565                 570                 575
Met Met Gly Arg Tyr Tyr Ala Ser Tyr Gly Glu Asn Val Val Ala Met
            580                 585                 590
Gly Phe Asn Leu Val Asp Ser His Asp Thr Ser Arg Val Leu Thr Asp
            595                 600                 605
Leu Gly Gly Gly Lys Leu Gly Asp Thr Pro Ser Asn Glu Ser Ile Gln
            610                 615                 620
Arg Leu Lys Leu Leu Ser Thr Leu Leu Tyr Ala Leu Pro Gly Thr Pro
```

-continued

```
              625                 630                 635                 640
Val Thr Phe Gln Gly Asp Glu Arg Gly Leu Leu Gly Asp Lys Gly His
                        645                 650                 655

Tyr Asp Glu Gln Arg Tyr Pro Ile Gln Trp Asp Thr Val Asn Glu Asp
                660                 665                 670

Val Leu Asn His Tyr Arg Ala Leu Ala Glu Leu Arg Lys Arg Val Pro
                675                 680                 685

Ala Leu Arg Ser Ser Ala Met Arg Phe Tyr Thr Ala Lys Gly Gly Val
        690                 695                 700

Met Ala Phe Phe Arg Gly His His Asp Glu Val Leu Val Val Ala Asn
705                 710                 715                 720

Ser Trp Lys Lys Pro Ala Leu Leu Glu Leu Pro Glu Gly Glu Trp Lys
                        725                 730                 735

Val Ile Trp Pro Glu Asp Phe Ser Pro Glu Leu Leu Arg Gly Thr Val
                740                 745                 750

Glu Val Pro Ala Ile Gly Ile Ile Ile Leu Glu Arg Gly
                755                 760                 765

<210> SEQ ID NO 3
<211> LENGTH: 31
<212> TYPE: DNA
<213> ORGANISM: Thermococcus kodakaraensis
<220> FEATURE:
<221> NAME/KEY: misc_feature
<222> LOCATION: (1)..(31)
<223> OTHER INFORMATION: 5' Primer

<400> SEQUENCE: 3
catatgagcg gatgtatctc ggagagcaac g                              31

<210> SEQ ID NO 4
<211> LENGTH: 25
<212> TYPE: DNA
<213> ORGANISM: Thermococcus kodakaraensis
<220> FEATURE:
<221> NAME/KEY: misc_feature
<222> LOCATION: (1)..(25)
<223> OTHER INFORMATION: 3' Primer

<400> SEQUENCE: 4
gaagcggggg tcaaccccgc tcaag                                     25
```